US010563254B2

(12) United States Patent
Lee et al.

(10) Patent No.: US 10,563,254 B2
(45) Date of Patent: Feb. 18, 2020

(54) NUCLEIC ACID AMPLIFICATION AND TESTING

(75) Inventors: Helen Hwai-an Lee, Cambridge (GB); Magda Anastassova Dineva, Cambridge (GB); Fiona Frances Sarah Fletcher-Brown, Haverhill (GB)

(73) Assignee: CAMBRIDGE ENTERPRISE LIMITED, Cambridge (GB)

(*) Notice: Subject to any disclaimer, the term of this patent is extended or adjusted under 35 U.S.C. 154(b) by 794 days.

(21) Appl. No.: 12/524,261

(22) PCT Filed: Jan. 23, 2008

(86) PCT No.: PCT/GB2008/000235
§ 371 (c)(1),
(2), (4) Date: Jan. 29, 2010

(87) PCT Pub. No.: WO2008/090340
PCT Pub. Date: Jul. 31, 2008

(65) Prior Publication Data
US 2010/0136542 A1 Jun. 3, 2010

(30) Foreign Application Priority Data
Jan. 23, 2007 (GB) .................. 0701253.7

(51) Int. Cl.
C12Q 1/68 (2018.01)
C12Q 1/6865 (2018.01)

(52) U.S. Cl.
CPC ................... *C12Q 1/6865* (2013.01)

(58) Field of Classification Search
None
See application file for complete search history.

(56) References Cited

U.S. PATENT DOCUMENTS

| 4,931,385 | A | | 6/1990 | Block et al. |
|---|---|---|---|---|
| 5,030,557 | A | | 7/1991 | Hogan et al. |
| 5,035,996 | A | | 7/1991 | Hartley |
| 5,102,788 | A | | 4/1992 | Cole |
| 5,130,238 | A | | 7/1992 | Malek et al. |
| 5,185,439 | A | | 2/1993 | Arnold, Jr. et al. |
| 5,283,174 | A | | 2/1994 | Arnold, Jr. et al. |
| 5,310,238 | A | | 5/1994 | Wheatley |
| 5,310,650 | A | | 5/1994 | McMahon et al. |
| 5,399,491 | A | | 3/1995 | Kacian et al. |
| 5,409,818 | A | | 4/1995 | Davey et al. |
| 5,437,990 | A | | 8/1995 | Burg et al. |
| 5,455,166 | A | | 10/1995 | Walker |
| 5,480,784 | A | | 1/1996 | Kacian et al. |
| 5,545,539 | A | | 8/1996 | Miller et al. |
| 5,554,517 | A | | 9/1996 | Davey et al. |
| 5,556,771 | A | * | 9/1996 | Shen et al. ............ 435/91.2 |
| 5,585,481 | A | | 12/1996 | Arnold, Jr. et al. |
| 5,593,824 | A | | 1/1997 | Treml et al. |
| 5,599,660 | A | * | 2/1997 | Ramanujam et al. ......... 435/4 |
| 5,612,200 | A | | 3/1997 | Dattagupta et al. |
| 5,614,387 | A | | 3/1997 | Shen et al. |
| 5,639,604 | A | | 6/1997 | Arnold, Jr. et al. |
| 5,654,142 | A | | 8/1997 | Kievits et al. |
| 5,656,207 | A | | 8/1997 | Woodhead et al. |
| 5,656,744 | A | | 8/1997 | Arnold, Jr. et al. |
| 5,658,737 | A | | 8/1997 | Nelson et al. |
| 5,674,680 | A | | 10/1997 | Saksela et al. |
| 5,696,251 | A | | 12/1997 | Arnold, Jr. et al. |
| 5,712,385 | A | | 1/1998 | McDonough et al. |
| 5,714,380 | A | | 2/1998 | Neri et al. |
| 5,750,338 | A | | 5/1998 | Collins et al. |
| 5,756,011 | A | | 5/1998 | Woodhead et al. |
| 5,756,709 | A | | 5/1998 | Nelson et al. |
| 5,766,849 | A | | 6/1998 | McDonough et al. |
| 5,780,219 | A | | 7/1998 | McDonough et al. |
| 5,824,518 | A | | 10/1998 | Kacian et al. |
| 5,827,646 | A | | 10/1998 | Nelson et al. |
| 5,827,656 | A | | 10/1998 | Nelson et al. |
| 5,834,254 | A | | 11/1998 | Shen et al. |
| 5,840,873 | A | | 11/1998 | Nelson et al. |
| 5,846,716 | A | | 12/1998 | Miller et al. |
| 5,856,088 | A | | 1/1999 | McDonough et al. |
| 5,861,251 | A | | 1/1999 | Park et al. |
| 5,876,992 | A | | 3/1999 | De Rosier et al. |
| 5,888,779 | A | | 3/1999 | Kacian et al. |

(Continued)

FOREIGN PATENT DOCUMENTS

| EP | 0 203 277 A2 | 12/1986 |
|---|---|---|
| EP | 0 265 244 A2 | 10/1987 |

(Continued)

OTHER PUBLICATIONS

Guatelli, J.C. et al., "Isothermal, in vitro Amplification of Nucleic Acids by a Multienzyme Reaction Modeled After Retroviral Replication" Proceedings of the National Academy of Sciences of the USA (1990) pp. 1874-1878, vol. 87 (19).

Fahy, E. et al., "Self-Sustained Sequence Replication (3SR): An Isothermal Transcription-Based Amplification System Alternative to PCR" PCR Methods and Applications (1991) pp. 25-33, vol. 1(1).

Van Gemen, B. et al., "Transcription Based Nucleic Acid Amplification Methods Like NASBA and 3SR Applied to Viral Diagnosis" Reviews in medical Virology (1995) pp. 205-211, vol. 5(4).

Cassol, S. et al., "Quantification of Human Immunodeficiency Virus Type 1 RNA from Dried Plasma Spots Collected on Filter Paper" Journal of Clinical Microbiology (1997) pp. 2795-2801, vol. 35(11).

Fakruddin, MD., et al., "Nucleic Acid Sequence Based Amplification (NASBA)-Prospects and Applications" Life Science Microbiology 2(1):L-106-L-121(2012).

(Continued)

*Primary Examiner* — Stephanie K Mummert

(74) *Attorney, Agent, or Firm* — Scully Scott Murphy & Presser, P.C.

(57) ABSTRACT

Methods for amplifying a target nucleic acid by self-sustained amplification methods are described. The methods are designed, in particular, to be carried out without use of specialised lab facilities or instruments. Compositions, lyophilised formulations, and kits for carrying out the methods are also described.

14 Claims, 8 Drawing Sheets

Specification includes a Sequence Listing.

(56) References Cited

U.S. PATENT DOCUMENTS

| | | | |
|---|---|---|---|
| 5,908,744 A | 6/1999 | McAllister et al. |
| 5,948,899 A | 9/1999 | Arnold, Jr. et al. |
| 5,955,261 A | 9/1999 | Kohne |
| 5,955,351 A | 9/1999 | Gerdes et al. |
| 5,968,781 A | 10/1999 | Yoon et al. |
| 5,981,183 A | 11/1999 | Takarada et al. |
| 6,001,558 A | 12/1999 | Backus et al. |
| 6,001,977 A | 12/1999 | Chang et al. |
| 6,004,745 A | 12/1999 | Arnold, Jr. et al. |
| 6,031,091 A | 2/2000 | Arnold, Jr. et al. |
| 6,063,603 A | 5/2000 | Davey et al. |
| 6,071,734 A | 6/2000 | Yoon et al. |
| 6,090,591 A | 7/2000 | Burg et al. |
| 6,110,678 A | 8/2000 | Weisburg et al. |
| 6,114,150 A | 9/2000 | Weissman et al. |
| 6,159,692 A | 12/2000 | Draper et al. |
| 6,245,519 B1 | 6/2001 | Brentano et al. |
| 6,252,059 B1 | 6/2001 | McDonough et al. |
| 6,261,773 B1 | 7/2001 | Segawa et al. |
| 6,277,561 B1 | 8/2001 | Guertler et al. |
| 6,280,952 B1 | 8/2001 | Weisburg et al. |
| 6,294,365 B1* | 9/2001 | De Rosier et al. ............ 435/188 |
| 6,300,056 B1 | 10/2001 | Irvine et al. |
| 6,300,068 B1 | 10/2001 | Burg et al. |
| 6,300,075 B1 | 10/2001 | Preston et al. |
| 6,303,293 B1 | 10/2001 | Patterson et al. |
| 6,303,306 B1 | 10/2001 | Takarada et al. |
| 6,410,273 B1 | 6/2002 | Crouzet et al. |
| 6,410,276 B1 | 6/2002 | Burg et al. |
| 6,414,152 B1 | 7/2002 | Campbell et al. |
| RE37,891 E | 10/2002 | Collins et al. |
| 6,458,556 B1 | 10/2002 | Hayashizaki |
| 6,485,982 B1 | 11/2002 | Charlton |
| 6,528,626 B2 | 3/2003 | Guertler et al. |
| 6,531,137 B2 | 3/2003 | Guertler et al. |
| 6,531,276 B1 | 3/2003 | Luciw et al. |
| 6,531,587 B2 | 3/2003 | Guertler et al. |
| 6,534,273 B2 | 3/2003 | Weisburg et al. |
| 6,551,824 B2 | 4/2003 | Guertler et al. |
| 6,589,734 B1 | 7/2003 | Kacian et al. |
| 6,610,476 B1 | 8/2003 | Chang et al. |
| 6,623,919 B1 | 9/2003 | Gorman et al. |
| 6,623,920 B1 | 9/2003 | Bee et al. |
| 6,649,749 B2 | 11/2003 | McDonough et al. |
| 6,773,915 B2 | 8/2004 | Guertler et al. |
| 6,821,724 B1 | 11/2004 | Mittman et al. |
| 6,858,712 B1 | 2/2005 | Chang et al. |
| 6,870,045 B2 | 3/2005 | Yang et al. |
| 6,881,537 B1 | 4/2005 | Goudsmit et al. |
| 6,949,368 B2 | 9/2005 | Chakrabarti et al. |
| 7,009,041 B1 | 3/2006 | McDonough et al. |
| 7,034,005 B2 | 4/2006 | Omura et al. |
| 7,083,922 B2 | 8/2006 | Kacian et al. |
| 7,097,979 B2 | 8/2006 | Bee et al. |
| 7,205,102 B1 | 4/2007 | Montagnier et al. |
| 7,217,508 B1 | 5/2007 | Wain-Hobson et al. |
| 7,232,654 B1 | 6/2007 | Chermann et al. |
| 7,276,357 B2 | 10/2007 | Chakrabarti et al. |
| 7,276,359 B1 | 10/2007 | Musunuri et al. |
| 7,374,927 B2 | 5/2008 | Palma et al. |
| 7,425,417 B2 | 9/2008 | Bee et al. |
| 7,585,625 B2 | 9/2009 | de Rooij et al. |
| 7,915,916 B2 | 3/2011 | Wilcox et al. |
| 8,576,992 B2 | 11/2013 | Samarasinghe |
| 2002/0062016 A1 | 5/2002 | McDonough et al. |
| 2002/0102575 A1 | 8/2002 | Auerbach |
| 2002/0155428 A1 | 10/2002 | Guertler et al. |
| 2002/0173016 A1 | 11/2002 | Wurst et al. |
| 2002/0177127 A1 | 11/2002 | Yang et al. |
| 2003/0039992 A1 | 2/2003 | Chakrabarti et al. |
| 2003/0157693 A1 | 8/2003 | Verdin et al. |
| 2003/0186900 A1 | 10/2003 | Omura et al. |
| 2004/0029111 A1 | 2/2004 | Linnen et al. |
| 2004/0038199 A1 | 2/2004 | Kleim et al. |
| 2004/0053223 A1 | 3/2004 | Bee et al. |
| 2005/0048531 A1 | 3/2005 | Mittman et al. |
| 2005/0069898 A1* | 3/2005 | Moon et al. ...................... 435/6 |
| 2005/0074792 A1 | 4/2005 | de Rooij et al. |
| 2005/0239118 A1 | 10/2005 | Goudsmit et al. |
| 2005/0272080 A1 | 12/2005 | Palma et al. |
| 2006/0068398 A1* | 3/2006 | McMillan .......................... 435/6 |
| 2006/0068399 A1 | 3/2006 | McMillan et al. |
| 2006/0223056 A1 | 10/2006 | Goudsmit et al. |
| 2006/0223057 A1 | 10/2006 | Goudsmit et al. |
| 2006/0228699 A1 | 10/2006 | Goudsmit et al. |
| 2007/0072279 A1 | 3/2007 | Meynial-Salles et al. |
| 2007/0087354 A1 | 4/2007 | Charneau et al. |
| 2008/0081328 A1 | 4/2008 | Linnen et al. |
| 2009/0062135 A1 | 3/2009 | Delfour et al. |
| 2009/0214589 A1 | 8/2009 | Despres et al. |
| 2010/0028382 A1 | 2/2010 | Charneau et al. |
| 2010/0041040 A1 | 2/2010 | Babiel et al. |
| 2010/0099078 A1 | 4/2010 | Van Baelen et al. |

FOREIGN PATENT DOCUMENTS

| | | |
|---|---|---|
| EP | 0 262 328 A2 | 4/1988 |
| EP | 0 310 229 A1 | 4/1989 |
| EP | 0 328 829 A2 | 8/1989 |
| EP | 0 387 696 A2 | 9/1990 |
| EP | 0 408 295 A2 | 1/1991 |
| EP | 0 587 298 A2 | 3/1994 |
| EP | 0 591 914 A2 | 4/1994 |
| EP | 0 617 132 A2 | 9/1994 |
| EP | 0 629 706 A2 | 12/1994 |
| EP | 0 682 120 A1 | 11/1995 |
| EP | 0 726 310 A1 | 8/1996 |
| EP | 0 731 174 A2 | 9/1996 |
| EP | 0 821 058 A2 | 1/1998 |
| EP | 0 878 553 A2 | 11/1998 |
| EP | 0 887 427 A2 | 12/1998 |
| EP | 0 978 570 A2 | 2/2000 |
| EP | 1 026 261 A2 | 8/2000 |
| EP | 1 026 263 A2 | 8/2000 |
| EP | 1 035 220 A2 | 9/2000 |
| EP | 1 050 587 A2 | 11/2000 |
| EP | 1 350 510 A1 | 10/2003 |
| EP | 1 422 298 A2 | 5/2004 |
| EP | 1 508 624 A1 | 2/2005 |
| EP | 1 568 787 A1 | 8/2005 |
| EP | 1 752 545 A2 | 2/2007 |
| EP | 1 783 232 A1 | 5/2007 |
| EP | 1 783 645 A1 | 5/2007 |
| EP | 2 020 444 A1 | 2/2009 |
| EP | 2 047 861 A1 | 4/2009 |
| EP | 2 130 929 A1 | 12/2009 |
| JP | 2000-279198 A | 10/2000 |
| JP | 2005-333959 A | 12/2005 |
| JP | 2006-238724 A | 9/2006 |
| JP | 2006-320237 A | 11/2006 |
| JP | 2007-135469 A | 6/2007 |
| JP | 2008-306962 A | 12/2008 |
| WO | WO 88/10315 A1 | 12/1988 |
| WO | WO 90/06995 A1 | 6/1990 |
| WO | WO 90/15159 A2 | 12/1990 |
| WO | WO 91/02818 A1 | 3/1991 |
| WO | WO 91/10746 A1 | 7/1991 |
| WO | WO 92/08800 A1 | 5/1992 |
| WO | 1993/00807 | 1/1993 |
| WO | WO 93/13223 A1 | 7/1993 |
| WO | WO 94/11507 A2 | 5/1994 |
| WO | WO 94/26934 A2 | 11/1994 |
| WO | WO 96/17083 A1 | 6/1996 |
| WO | WO 96/32497 A1 | 10/1996 |
| WO | WO 99/07898 A1 | 2/1999 |
| WO | WO 99/37805 A1 | 7/1999 |
| WO | 1999/45966 | 9/1999 |
| WO | WO 00/68436 A1 | 11/2000 |
| WO | WO 01/04361 A2 | 1/2001 |
| WO | WO 01/79542 A2 | 10/2001 |
| WO | 2002/04667 A2 | 1/2002 |
| WO | WO 02/04668 A2 | 1/2002 |
| WO | WO 02/04669 A2 | 1/2002 |
| WO | WO 02/04671 A2 | 1/2002 |

(56) References Cited

FOREIGN PATENT DOCUMENTS

| | | |
|---|---|---|
| WO | WO 02/34951 A1 | 5/2002 |
| WO | WO 02/34951 A2 | 5/2002 |
| WO | WO 03/020964 A1 | 3/2003 |
| WO | WO 03/080869 A2 | 10/2003 |
| WO | WO 03/106714 A1 | 12/2003 |
| WO | WO 2005/019479 A1 | 3/2005 |
| WO | WO 2005/071401 A2 | 8/2005 |
| WO | WO 2005/111221 A1 | 11/2005 |
| WO | WO2005103277 * 11/2005 ............... C12Q 1/68 |
| WO | 2006003439 A2 | 1/2006 |
| WO | 2006/011667 A1 | 2/2006 |
| WO | WO 2006/036845 A1 | 4/2006 |
| WO | WO 2006/036848 A2 | 4/2006 |
| WO | 2006/046265 A1 | 5/2006 |
| WO | 2006/119280 A2 | 11/2006 |
| WO | 2007/005626 A1 | 1/2007 |
| WO | WO 2007/052165 A2 | 5/2007 |
| WO | WO 2007/054520 A2 | 5/2007 |
| WO | WO 2008/053478 A2 | 5/2008 |
| WO | WO 2008/090185 A1 | 7/2008 |
| WO | WO 2009/019612 A2 | 2/2009 |

OTHER PUBLICATIONS

Koonjul, P. K., et al., "Inclusion of polyvinylpyrrolidone in the polymerase chain reaction reverses the inhibitory effects of polyphenolic contamination of RNA" Nucleic Acids Research 27(3):915-916 (1999).

European Office Action dated Sep. 21, 2016 issued in European Patent Application No. 08 701 909.7.

Winship, P.R., "An improved method for directly sequencing PCR amplified material using dimethyl sulphoxide", Nucleic Acids Research, (1989), vol. 17, No. 3, 1 page.

Boom, R. et al., "Rapid and Simple Method for Purification of Nucleic Acids", Journal of Clinical Microbiology, (Mar. 1990), vol. 28, No. 3, pp. 495-503.

Chiou, S., "DNA-Scission Activities of Ascorbate in the Presence of Metal Chelates", J. Biochem., (1984), No. 96, pp. 1307-1310.

Chomczynski, P. et al., "Single-Step Method of RNA Isolation by Acid Guanidinium Thiocyanate-Phenol-Chloroform Extraction", Analytical Biochemistry, (1987), vol. 162, pp. 156-159.

Dineva, M.A. et al., "Simultaneous Visual Detection of Multiple Viral Amplicons by Dipstick Assay", Journal of Clinical Microbiology, (Aug. 2005), vol. 43, No. 8, pp. 4015-4021.

Gen-Probe APTIMA General Purpose Reagents (GPR) 250 Kit for Laboratory Use., www.gen-probe.com, (2005), 2 pages.

Kievits, T. et al., "NASBA isothermal enzymatic in vitro nucleic acid amplification optimized for the diagnosis of HIV-1 infection", Journal of Virological Methods, (1991), vol. 35, pp. 273-286.

Nakahara, K. et al., "Inosine 5'-triphosphate can dramatically increase the yield of NASBA products targeting GC-rich and intramolecular base-paired viroid RNA", Nucleic Acids Research, (1998), vol. 26, No. 7, pp. 1854-1855.

Compton, J., "Nucleic acid sequence-based amplification", Nature, (Mar. 7, 1991), vol. 350, pp. 91-92.

Schnoor, M. et al., "Characterization of the synthetic compatible solute homoectoine as a potent PCR enhancer", Biochemical and Biophysical Research Communications, (2004), No. 322, pp. 867-872.

Weissensteiner, T. et al., "Strategy for Controlling Preferential Amplification and Avoiding False Negatives in PCR Typing", BioTechniques, (Dec. 1996), vol. 21, pp. 1102-1108.

High Pure Viral Nucleic Acid Kit for isolation of viral nucleic acids for PCR or RT-PCR, Cat. No. 1 858 874, Version 6, Mar. 2002, 2 pages.

Sigman, D.S. et al., "Oxygen-dependent Cleavage of DNA by the 1,10-Phenanthroline Cuprous Complex", The Journal of Biological Chemistry, (Dec. 25, 1979), vol. 254, No. 24, pp. 12269-12272.

Vogelstein, B. et al., "Preparative and analytical purification of DNA from agarose", Proc. Natl. Acad. Sci. USA, (Feb. 1979), vol. 76, No. 2, pp. 615-619.

Walker, G.T. et al., "Isothermal in vitro amplification of DNA by a restriction enzyme/DNA polymerase system", Proc. Natl. Acad. Sci. USA, (Jan. 1992), vol. 89, pp. 392-396.

De Bar, M. P., "The Impact of HIV-1 Subtypes on Molecular Diagnostics", Extract from Thesis, (2000), 3 pages.

EP Office Action dated Sep. 10, 2018 issued in corresponding EP Application No. 12 169 640.5.

Kaijalainen S. et al., "An alternative hot start technique for PCR in small volumes using beads of wax-embedded reaction components dried in trehalose", Nucleic Acids Research (1993), vol. 21, No. 12, pp. 2959-2960.

* cited by examiner

Total assay time: 80 minutes

Note: Steps 1-3 could be substituted with any sample preparation procedure using a commercially available kit for nucleic acid extraction

Figure 3

| HIV RNA load (copies/ml): | $10^5$ | $10^4$ | $5\times10^3$ | $10^3$ | $5\times10^2$ | $2\times10^2$ | 0 |
|---|---|---|---|---|---|---|---|
| Test line signal | | | | | | | |
| Signal intensity | 5.0 | 4.5 | 4.0 | 3.0 | 2.0 | 0.5 | 0 |

Figure 4

SAMBA-NAT detection of *Chlamydia trachomatis*

| *Chlamydia trachomatis* (copies/test) | $10^4$ | $2 \times 10^3$ | 750 | 200 | 50 | 0 |
|---|---|---|---|---|---|---|
| Readout line | | | | | | |
| Signal intensity | 5 | 4.5 | 4 | 3 | 2 | 0 |

Figure 5

| HIV load, (copies /ml) | $10^5$ | $10^4$ | $10^3$ | $2\times10^2$ | 0 |
|---|---|---|---|---|---|
| SAMBA-NAT | | | | | |
| Commercial NASBA-NAT | | | | | |

SEQUENCE LISTING

<160> NUMBER OF SEQ ID NOS: 9

<210> SEQ ID NO 1
<211> LENGTH: 21
<212> TYPE: DNA
<213> ORGANISM: Artificial
<220> FEATURE:
<223> OTHER INFORMATION: Sense primer

<400> SEQUENCE: 1
cctcaataaa gcttgccttg a                                              21

<210> SEQ ID NO 2
<211> LENGTH: 17
<212> TYPE: DNA
<213> ORGANISM: Artificial
<220> FEATURE:
<223> OTHER INFORMATION: Antisense primer

<400> SEQUENCE: 2
ggcgccactg ctagaga                                                   17

<210> SEQ ID NO 3
<211> LENGTH: 20
<212> TYPE: DNA
<213> ORGANISM: Artificial
<220> FEATURE:
<223> OTHER INFORMATION: Detector probe

<400> SEQUENCE: 3
ctcaataaag cttgccttga                                                20

<210> SEQ ID NO 4
<211> LENGTH: 20
<212> TYPE: DNA
<213> ORGANISM: Artificial
<220> FEATURE:
<223> OTHER INFORMATION: Capture probe

<400> SEQUENCE: 4
cgtctgttgt gtgactctgg                                                20

<210> SEQ ID NO 5
<211> LENGTH: 21
<212> TYPE: DNA
<213> ORGANISM: Artificial
<220> FEATURE:
<223> OTHER INFORMATION: Helper probe

<400> SEQUENCE: 5
gtgcttcaag tagtgtgtgc c                                              21

<210> SEQ ID NO 6
<211> LENGTH: 20
<212> TYPE: DNA
<213> ORGANISM: Artificial
<220> FEATURE:
<223> OTHER INFORMATION: Sense primer

<400> SEQUENCE: 6
agcaattgtt tcgacgattg                                                20

<210> SEQ ID NO 7
<211> LENGTH: 20
<212> TYPE: DNA
<213> ORGANISM: Artificial

```
<220> FEATURE:
<223> OTHER INFORMATION: Antisense primer

<400> SEQUENCE: 7
cacatagact ctcccttaac                                                   20

<210> SEQ ID NO 8
<211> LENGTH: 22
<212> TYPE: DNA
<213> ORGANISM: Artificial
<220> FEATURE:
<223> OTHER INFORMATION: Detector probe

<400> SEQUENCE: 8
aacttgggaa taacggttgg aa                                                22

<210> SEQ ID NO 9
<211> LENGTH: 21
<212> TYPE: DNA
<213> ORGANISM: Artificial
<220> FEATURE:
<223> OTHER INFORMATION: Capture probe

<400> SEQUENCE: 9
cgctaatacc gaatgtggcg a                                                 21
```

NUCLEIC ACID AMPLIFICATION AND TESTING

This invention relates to methods for amplifying a target nucleic acid, and to methods for nucleic acid testing, particularly methods that can be carried out without specialised lab facilities or instruments. Compositions, formulations, and kits for nucleic acid amplification are also provided, as well as lyophilised formulations and kits comprising lyophilised formulations.

Nucleic acid testing is used for many purposes such as screening and diagnosis of infectious diseases and genetic disorders, testing for disease susceptibility, monitoring progression of treatment, and improving the safety of blood supplies. Nucleic acid testing combines the advantages of direct and highly sequence-specific detection of nucleic acid of an infectious agent with an analytic sensitivity that is several orders of magnitude higher than that of immuno-based tests, or virus isolation and cell culture methods. Nucleic acid testing also reduces the risk of infectious agent transmission between infection and seroconversion, of infection with immunovariant viruses, and of immunosilent or occult carriage.

Well known methods of nucleic acid testing involve use of reverse transcription of RNA followed by PCR(RT-PCR) to amplify RNA species. However, RT-PCR suffers from the disadvantage that it involves repeated wide changes in sample temperature, for which specialised thermal cycling instruments are required. A further disadvantage is that amplified RNA template can be difficult to differentiate from amplified contaminating double stranded DNA.

An alternative RNA amplification strategy to RT-PCR is termed transcription-based amplification. Such methods involve amplification of an RNA template using reverse transcriptase (RT), RNase H, and RNA polymerase activities, and include nucleic acid sequence-based amplification (NASBA), transcription-mediated amplification (TMA), and self-sustained sequence replication (3SR) (Chan and Fox, Rev. Med. Microbiol. 10: 185-196 (1999); Guatelli et al., Proc. Natl. Acad. Sci. 87: 1874-1878 (1990); Compton, Nature 350:91-92 (1991)). NASBA and 3SR use RT from Avian Myeloblastosis Virus (AMV) (which also has RNaseH activity), RNase H from $E.$ $coli$, and T7 RNA polymerase. TMA uses Moloney Murine Leukemia Virus (MMLV) RT (which also has RNase H activity), and T7 RNA polymerase.

Transcription-based amplification methods have several advantages over RT-PCR. The reactions occur simultaneously in a single tube, and are carried out under isothermal conditions so a thermocycler is not required. The amplification reaction is faster than RT-PCR ($1\times10^9$-fold amplification can be seen after five cycles, compared with $1\times10^6$-fold amplification after 20 cycles for RT-PCR). DNA background does not interfere with transcription-based amplification, and so these methods are not affected by double stranded DNA contamination. The amplification product is single stranded and can be detected without any requirement for strand separation.

Conventional transcription-based amplification methods, however, suffer from the disadvantage that they have lower specificity than RT-PCR. It is also necessary to denature the nucleic acid template by heating the sample, and then cooling before adding the enzymes required for amplification of the template, thereby increasing the complexity of the method. Transcription-based amplification methods are also not as robust as RT-PCR. Conventional NASBA is sensitive to temperature fluctuations exceeding +/−0.5° C.

U.S. Pat. No. 5,981,183 describes a method of transcription-based amplification which uses thermostable enzymes. The amplification reaction is carried out at 50-70° C., thereby improving specificity. However, a disadvantage of this method is that it is still susceptible to false positives caused by false priming of denatured double stranded DNA. Such methods are also not well suited to use in the field because of the need to heat the reaction to 50-70° C.

A further disadvantage of conventional nucleic acid testing is that detection of the amplified reaction product requires time-consuming, labour-intensive electrophoretic separation of the reaction products, or expensive equipment to detect fluorescent or chemiluminescent signals. The reagents required are expensive and must be transported and stored below room temperature. Separate designated areas are required for the sample preparation, amplification, and detection steps of the methods. The methods can only be carried out in specialized, well-equipped laboratories, by highly trained technicians. Consequently, conventional methods are not suitable for near-patient or field testing, and are unaffordable in poorer regions with a high prevalence of infectious disease (such as Africa, Asia, and Latin America) where they are most needed.

There is, therefore, a need to provide methods of nucleic acid testing that can be carried out without use of specialised lab facilities or instruments, and which have high specificity for target nucleic acid.

Lyophilisation has been used to store enzymes for nucleic acid amplification reactions. U.S. Pat. No. 5,556,771 describes lyophilised formulations that comprise MMLV RT and T7 polymerase with trehalose and polyvinyl pyrrolidine as cryoprotectant stabilizing agents. However, the results described in U.S. Pat. No. 5,556,771 show some loss in activity (measured as the ability to cause nucleic acid amplification) after storage at 35° C. for 61 days. Instructions provided with commercially available kits comprising lyophilised reagents for carrying out transcription-mediated amplification (GEN-PROBE® APTIMA® General Purpose Reagents (GPR) 250 Kit) or PCR amplification (Smart-Mix™ HM of Cepheid) require the lyophilised reagents to be stored at 2-8° C. Instructions provided with a commercially available kit containing lyophilised reagents for NASBA-based nucleic acid amplification (Nuclisens® Basic Kit Amplification Reagents of Biomérieux) specifies that the amplification reagents should be stored at ≤−20° C. We have also found that lyophilised formulations disclosed in U.S. Pat. No. 5,556,771 and in the above commercially available kits do not reconstitute rapidly, but instead require extensive mixing in specially formulated reconstitution buffers.

There is, therefore, a need to provide lyophilised formulations that can preserve labile reagents in a stable condition for long periods at ambient temperature, and which can be easily and rapidly rehydrated.

According to the invention there is provided a method of nucleic acid amplification, which comprises amplifying a target nucleic acid by a self-sustained amplification reaction which is carried out at a temperature between 42° C. and 50° C.

The term "self-sustained amplification reaction" is used herein to include nucleic acid amplification reactions in which copies of a target nucleic acid are produced, which then function as templates for production of further copies of target nucleic acid (either sense or anti-sense copies). The reactions are self-sustained reactions that can occur under isothermal conditions, and so there is no requirement for thermal cycling during the amplification reaction (unlike, for example, the polymerase chain reaction (PCR)). Examples of self-sustained amplification reactions are known to the skilled person, and include transcription-based amplifications, strand displacement amplification (SDA), rolling-circle amplification (RCA), Q beta replicase amplification, and loop-mediated isothermal amplification (LAMP).

It has been found that the time taken to obtain a desired copy number of amplification product using a method of the invention is surprisingly much less than the time taken to achieve the same copy number with conventional self-sustained amplification methods. In our experience, methods of the invention are approximately twice as quick as conventional methods. A suitable incubation time at between 42° C. and 50° C. is at least 30 minutes, or at least 40 minutes. 45-55 minutes may be optimal.

Whilst the temperature may vary between 42° C. and 50° C. when carrying out the amplification reaction, it is expected that the amplification reaction will generally be carried out under substantially isothermal conditions, i.e. within a temperature range of 1-3° C. A suitable way of achieving this is to incubate the amplification reaction using a water bath.

The phrase "at a temperature between 42° C. and 50° C." means above 42° C. and less than 50° C. The self-sustained amplification reaction may be carried out at a temperature above 43° C. and less than 50° C. The self-sustained amplification reaction may be carried out at a temperature of 43-49° C. The reaction may be carried out at a temperature of 43-49° C., 44-49° C., 45-49° C., or 45-48° C.

The target nucleic acid may be DNA (single or double stranded) or RNA. The target nucleic acid may be any target nucleic acid that it is desired to amplify or detect, including ribosomal RNA, viral or bacterial RNA or DNA. The target nucleic acid may be nucleic acid of (or derived from) a disease causing micro-organism (for example HCV). The target nucleic acid may be nucleic acid of an organism associated with a sexually transmitted disease, such as *Chlamydia trachomatis*, or HIV. In other embodiments, the target nucleic acid may be nucleic acid of a subject (for example to determine a particular genotype of the subject).

Methods of the invention may be used to determine whether or not a target nucleic acid is present in a sample solution suspected of containing the target nucleic acid. Accordingly, there is also provided according to the invention a method of testing for the presence of a target nucleic acid in a sample solution suspected of containing the target nucleic acid, the method comprising incubating the sample solution under conditions for amplification of the target nucleic acid by a self-sustained amplification reaction at a temperature between 42° C. and 50° C.

The sample solution may be any solution suspected of containing a target nucleic acid which it is desired to detect. The sample solution may be, or be derived from, a biological sample obtained from a subject. Examples of biological samples are blood, serum, urine, a cervical smear, a swab sample, or tissue homogenate.

It will be appreciated that it may be necessary to extract nucleic acid from the biological sample to provide a sample solution that can be tested in accordance with the invention to determine whether or not a target nucleic acid is present. Nucleic acid extraction may be carried out using any suitable nucleic acid extraction method. Suitable methods include solid phase extraction of nucleic acid on silica particles (Boom et al., J. Clin. Microbiol; 28:495-503, 1990) or silica gel/glass fibre filters (Vogelstein et al., Proc. Natl. Acad. Sci., 76: 615-619, 1979) in the presence of chaotropic salts, using commercially available kits (for example from Qiagen, Roche, or Invitrogen). Alternative methods include: liquid phase extraction technology based in acid guanidinium thiocyanate-phenol-chloroform extraction (Chomczynski et al., Anal Biochemistry; 162: 156-159, 1987); FTA® kit protocol by Whatmann using FTA® paper filter matrixes impregnated by chemical formula that lyses cell membranes and immobilizes the nucleic acids; Charge Switch™ technology (Baker et al., EP1036082). Alternative, more simple procedures involve sample lysis by heat or chemical treatment and sample dilution prior to amplification.

Methods of the invention for determining whether or not a target nucleic acid is present in a sample solution may be used to test a biological sample obtained from a subject to see whether the subject is infected with an infectious agent, or to monitor the subject for progression of a disease, or for response to treatment.

Examples of infectious agents include bacterial or viral infectious agents, such as HIV, HCV, HPV, CMV, HTLV, EBV, rhinovirus, measles virus. Infectious agents may be those associated with sexually transmitted disease, such as *Chlamydia trachomatis*, or HIV.

Suitable self-sustained nucleic acid amplification reactions may be carried out using the following enzyme activities: an RNA-dependent DNA polymerase, a DNA-dependent DNA polymerase, a DNA/RNA duplex-specific ribonuclease, and a DNA-dependent RNA polymerase.

The RNA-dependent DNA polymerase, DNA-dependent DNA polymerase, and DNA/RNA duplex-specific ribonuclease activities may be provided by a single enzyme (for example AMV-RT or MMLV-RT). Additional DNA/RNA duplex-specific ribonuclease activity may be provided by a separate enzyme (for example an RNaseH). In some embodiments, AMV-RT and RNaseH may be used (as in NASBA).

As explained above, self-sustained nucleic acid amplification reactions are known to the skilled person. Suitable types of reaction that may be used in accordance with the invention include transcription-based amplification methods, such as methods corresponding to NASBA, TMA, or 3SR (i.e. methods which are the same as conventional NASBA, TMA, or 3SR, but carried out at a temperature between 42° C. and 50° C.).

A transcription-based self-sustained amplification reaction suitable for use in methods of the invention is described below, with reference to FIG. 1.

An antisense Primer 1 comprises nucleic acid sequence complementary to a portion of a target RNA so that the primer can hybridise specifically to the target RNA, and a single stranded-version of a promoter sequence for a DNA-dependent RNA polymerase at its 5'-end. Primer 1 is annealed to the RNA target. An RNA-dependent DNA polymerase extends Primer 1 to synthesise a complementary DNA (cDNA) copy of the RNA target. A DNA/RNA duplex-specific ribonuclease digests the RNA of the RNA-cDNA hybrid. A sense Primer 2 comprises nucleic acid sequence complementary to a portion of the cDNA. Primer 2 is annealed to the cDNA downstream of the part of the cDNA formed by Primer 1. Primer 2 is extended by a DNA-dependent DNA polymerase to produce a second DNA strand which extends through the DNA-dependent RNA polymerase promoter sequence at one end (thereby forming a double stranded promoter). This promoter is used by a DNA-dependent RNA polymerase to synthesise a large number of RNAs complementary to the original target sequence. These RNA products then function as templates for a cyclic phase of the reaction, but with the primer annealing steps reversed, i.e., Primer 2 followed by Primer 1.

In a variation of this method, Primer 2 may also include a single stranded version of a promoter sequence for the DNA-dependent RNA polymerase. This results in production of RNAs with the same sense as the original target sequence (as well as RNAs complementary to the original target sequence).

In some conventional self-sustained transcription-based amplification reactions it is known to cleave the target RNA at the 5'-end before it serves as the template for cDNA synthesis. An enzyme with RNase H activity is used to cleave the RNA portion of an RNA-DNA hybrid formed by adding an oligonucleotide (a cleavage oligonucleotide) having a sequence complementary to the region overlapping and adjacent to the 5'-end of the target RNA. The cleavage oligonucleotide may have its 3'-terminal-OH appropriately modified to prevent extension reaction. Whilst in some embodiments of the invention a cleavage oligonucleotide could be used, it is preferred that a method of the invention is carried out in the absence of a cleavage oligonucleotide thereby simplifying the amplification reaction and the components required.

It will be appreciated that in addition to the required enzyme activities, it will also be necessary to provide appropriate nucleotide triphosphates (for transcription-based amplifications ribonucleotide triphosphates (rNTPs, i.e. rATP, rGTP, rCTP, and rUTP), and deoxyribonucleotide triphosphates (dNTPs, i.e. dATP, dGTP, dCTP, and dTTP) are required), appropriate primers for specific amplification of the target nucleic acid, a suitable buffer for carrying out the amplification reaction, and any necessary cofactors (for example magnesium ions) required by the enzyme activities. Examples of suitable buffers include Tris-HCl, HEPES, or acetate buffer.

Accordingly, conditions for amplification of the target nucleic acid used in methods of the invention for testing for the presence of a target nucleic acid in a sample solution may comprise enzyme activities required for the self-sustained amplification reaction (for example, RNA-dependent DNA polymerase, DNA-dependent DNA polymerase, DNA/RNA duplex-specific ribonuclease, and DNA-dependent RNA polymerase enzyme activities), cofactors required by the enzyme activities (for example magnesium ions), primers for specific amplification of the target nucleic acid, appropriate nucleotide triphosphates (ribonucleotide triphosphates and deoxyribonucleotide triphosphates are required for transcription-based amplifications). Conditions for amplification of the target nucleic acid should also include a suitable buffer (such as Tris-HCl, HEPES, or acetate buffer). A suitable salt may be provided, such as potassium chloride or sodium chloride.

Suitable concentrations of these components may readily be determined by the skilled person. We have found that suitable rNTP concentrations are typically in the range 0.25-5 mM, preferably 0.5-2.5 mM. Suitable dNTP concentrations are typically in the range 0.25-5 mM dNTP, preferably 0.5-2.5 mM. Suitable magnesium ion concentrations are typically in the range 5-15 mM.

Whilst it is possible that the self-sustained amplification reaction may be carried out in the temperature range of between 42° C. and 50° C. using thermostable enzymes, the Applicant has appreciated that non-thermostable enzymes may be used in this temperature range (provided the non-thermostable enzyme retains activity between 42 and 50° C.). The term "thermostable enzyme" is used herein to mean an enzyme with optimal enzymatic activity at 50° C. or above. Typically a thermostable enzyme maintains its activity at temperatures at least in excess of 55° C. and up to about 72° C. or higher. A "non-thermostable enzyme" has optimal enzymatic activity below 50° C., suitably in the temperature range of 37-41° C. (although the non-thermostable enzyme may still retain activity at 50° C. or above). Accordingly, in certain embodiments of the invention, at least one of the enzyme activities (for example the DNA-dependent RNA polymerase activity) is provided by a non-thermostable enzyme. In some embodiments, all of the enzyme activities use for the amplification reaction may be provided by non-thermostable enzymes. Use of non-thermostable enzymes is preferred because this allows the amplification reaction to proceed efficiently at a temperature between 42° C. and 50° C. Thermostable enzymes generally have optimum activity at temperatures above this range.

Some conventional transcription-based amplification methods use very high amounts of T7 RNA polymerase (for example 142 or more units, where one unit incorporates 1 nmole of labelled nucleotide into acid insoluble material in 1 hour at 37° C. under standard assay conditions, such as: 40 mM Tris-HCl (pH8.0), 50 mM NaCl, 8 mM MgCl$_2$, 5 mM DTT, 400 μM rNTPs, 400 μM [$^3$H]-UTP(30 cpm/pmoles), 20 μg/ml T7 DNA, 50 μg/ml BSA, 100 μl reaction volume, 37° C., 10 min.). We have found that methods of the invention can be carried out using significantly less T7 RNA polymerase than such conventional methods, thereby reducing cost. Thus, methods of the invention are preferably carried out using less than 142 units of a DNA-dependent RNA polymerase (for example T7 RNA polymerase), suitably less than 100 units or less than 50 units, such as 30-40 units.

It may be desirable to include one or more agents that may facilitate or enhance the self-sustained amplification reaction at temperatures between 42° C. and 50° C. An agent may facilitate or enhance the reaction by any mechanism, but typically the agent is not essential for the reaction to take place, and may not directly take part in the reaction. Some such agents may act by helping to stabilize the activity of an enzyme required for the self-sustained amplification reaction between 42° C. and 50° C., or by reducing the effect of any inhibitors of the self-sustained amplification reaction that may be present.

Examples of suitable agents include the following:
  i) an inert protein. The term "inert protein" is used herein to mean a protein which does not take part in the amplification reaction. Suitable examples include bovine serum albumin (BSA), casein, gelatin, or lysozyme. A suitable concentration range of the inert protein is 0.01-1 μg/μl. A The protein should be RNase-free;
  ii) a reducing agent, such as Dithiothreitol (DTT) (for example at a concentration of 1-5 mM) or n-acetylcysteine (NAC) (for example at a concentration of 0.1-1M);
  iii) an inert amphiphilic polymer (which is not a protein). The term "inert amphiphilic polymer" is used herein to mean an amphiphilic polymer which does not take part in the amplification reaction. The inert amphiphilic polymer may be non-charged. Examples of inert amphiphilic polymers are polyvinyl pyrrolidone (PVP) and polyethylene glycol (PEG) or other similar polyole. A suitable concentration range of the inert amphiphilic polymer is 0.1-2%;

iv) a sugar-alcohol, for example sorbitol, mannitol, or glycerol (for example up to 5% glycerol). A suitable concentration range is 0.1-2 M;
v) a low molecular weight saccharide, suitably a monosaccharide, disaccharide, or trisaccharide. Examples of disaccharides are trehalose, sucrose and maltose. A suitable concentration range is 2.5%-15%;
vi) homopolymeric nucleic acid (200-2000 bases). Examples include: Poly A, Poly C, or Poly U nucleic acid (for example at 100-600 ng/amplification); poly dA, poly dC or poly dI (for example at 100-600 ng/amplification); tRNA; rRNA;
vii) acetate salts, for example magnesium or potassium acetate;
viii) spermidine, for example at 0.5-3 mM;
ix) poly-Lysine, for example at 0.2-3 mM;
x) detergent, for example NP40 or Tween20 (suitably at 0.01-0.5%).

The concentration of each of the above agents may be optimised for each different target nucleic acid and set of primers used for amplification.

Other agents may act by facilitating primer annealing or facilitating denaturation of double stranded nucleic acid. Accordingly, it may be desired alternatively or additionally to include in the amplification reaction one or more agents that facilitate primer annealing and/or one or more agents that facilitate denaturation of double stranded nucleic acid.

Examples of agents that facilitate primer annealing are positively charged ions, such as potassium or sodium ions. Potassium ion may be provided by potassium chloride or acetate (suitably at a concentration of 30-200 mM or 30-90 mM). Sodium ion may be provided by sodium chloride or acetate (suitably at a concentration of 50-400 mM).

Examples of agents that facilitate denaturation of double stranded nucleic acid are:
i) polar aprotic solvents, such as dimethyl sulfoxide (DMSO), for example at a concentration of 3-20% (v/v), or less than 10% (v/v). It has been found that when nucleic acid amplification is carried out in the temperature range of between 42 and 50° C., the amount of polar aprotic solvent required to have an effect is less than the amount required at lower temperatures. Alternative polar aprotic solvents that may be used include tetramethylene sulfone, or tetramethylene sulfoxide;
ii) a zwitterionic compound, such as betaine (N,N,N-trimethylglycine), for example at a concentration of 0.2-3M. Betaine may be used in place of DMSO. An advantage of betaine is that it is more stable than DMSO, and it does not appear to inhibit lyophilisation. Consequently, use of betaine instead of DMSO may be suitable where lyophilised reagents are used for the amplification reaction. In some circumstances, however, use of betaine and DMSO may be desired since synergistic effects of these reagents on double stranded nucleic acid denaturation have been observed. Alternative zwitterionic compounds that may be used include monomethylglycine, dimethylglycine, D-carnitine, homoectoine, L-ectoine or derivatives;
iii) a modified nucleotide triphosphate (NTP) that comprises a base that can base pair with guanine or cytosine such that the melting temperature of the base pair is less than the melting temperature of a guanine-cytosine base pair. An example of a modified NTP is inosine triphosphate (rITP). An inosine-cytosine (I-C) base pair comprises two hydrogen bonds between the bases, compared with a guanine-cytosine (G-C) base pair which comprises three hydrogen bonds, and so the melting temperature of the I-C base pair is less than a G-C base pair. For example, rITP may be present in the amplification reaction at a concentration of 0.5-4 mM or 0.5-3.5 mM. When rITP is present, the amount of rGTP in the amplification reaction may be reduced compared to the amounts of the other ribonucleotide triphosphates (rATP, rCTP, rUTP) to compensate for the amount of rITP. The ratio of rITP:rGTP will depend on the target nucleic acid and on the primers that are used. A typical ratio is 1:3 to 1:1.5 rITP:rGTP;
iv) a single-stranded nucleic acid binding protein, such as Single-stranded Binding Protein (SSB), or Phage T4 gene 32 protein. SSB and Phage T4 gene 32 protein bind single stranded regions of DNA and thereby inhibit formation of double stranded DNA or DNA/RNA hybrids.

Other agents may improve the specificity of the amplification reaction. Accordingly, it may be desired alternatively or additionally to include one or more such agents in the amplification reaction.

Examples of agents that may improve the specificity of the amplification reaction are:
i) ammonium ions, such as tetramethylammonium chloride (TMAC). Ammonium ions are thought to interfere with week hydrogen bond formation and create more stringent and specific hybridisation conditions;
ii) EDTA, EGTA, nitroacetic acid (NTA), uramil diacetic acid (UDA), trans-1,2-cyclohexanediaminetetraacetic acid (CyDTA), diethylenetriaminepentaacetic acid (DPTA), ethyleneglycolbis(2-aminoethyl)ether diaminetetraacetic acid (GEDTA), triethylenetetraminehexaacetic acid (TTHA), or a salt thereof. These compounds are believed to improve the signal-to-noise ratio of amplification reactions by significantly inhibiting the occurrence of non-specific amplification reactions;
iii) carrier nucleic acid with one or more magnesium salts. This is believed to reduce polymerase extension of non-target nucleic acids during amplification through a reduction in the amount of primer-dimer formation.

In conventional transcription-based amplification methods, it is generally necessary to carry out an initial incubation of sample containing the target nucleic acid at a raised temperature before cooling the sample. This reduces secondary structure in the target nucleic acid, and allows primers for use in the amplification reaction to anneal to the target nucleic acid. Unless enzymes are used that retain activity after incubation at the raised temperature, this initial incubation step is carried out before addition of the enzymes required for the amplification reaction.

It has been found, however, that carrying out the self-sustained amplification reaction at a temperature between 42° C. and 50° C. does not require a preliminary raised temperature incubation step to be carried out. Consequently, methods of the invention are simplified compared to conventional transcription-based amplification methods, and can be carried out more rapidly than such methods. These are particularly important advantages for nucleic acid amplification reactions carried out in the field.

Of course, in some circumstances, it may nonetheless be desirable to carry out a raised temperature pre-incubation step. If the target nucleic acid is double stranded DNA, it will usually be necessary to denature the target before carrying out the amplification reaction. Double stranded DNA may be denatured by chemical methods well known to the skilled person, or alternatively by raised temperature denaturation.

Once the amplification reaction has been carried out, it will usually be desired to detect product of the amplification reaction (referred to as "amplification product" below).

Single or double stranded amplification product may be detected. For example, double stranded amplification product produced during the cyclic phase of the self-sustained amplification reaction illustrated in FIG. 1 and described above may be detected. If single stranded amplification product is detected this removes any requirement for separation of double strands, and therefore simplifies detection.

Detection of amplification product may be carried out using any suitable method. For example, an instrument-independent detection method may be used, for example allowing visual detection of the amplification product.

According to particular embodiments of the invention amplification product may be detected using a dipstick. In suitable methods of dipstick detection, amplification product is transported along a dipstick by capillary action to a capture zone of the dipstick, and detected at the capture zone. Amplification product may be captured and detected using a sandwich nucleic acid dipstick detection assay in which the amplification product is immobilised at the capture zone of the dipstick by hybridisation to a capture probe, and detected at the capture zone by hybridisation to a detection probe.

Methods of detection of nucleic acid by dipstick assay are known to the skilled person. The Applicant has developed particularly sensitive methods of dipstick detection, which are described in WO 02/004667, WO 02/04668, WO 02/004669, WO 02/04671, and in Dineva et al (Journal of Clinical Microbiology, 2005, Vol. 43(8): 4015-4021).

It is well known that a disadvantage of conventional nucleic acid amplification reactions is the risk of contamination of target nucleic acid with non-target nucleic acid that can lead to false positives. Conventionally, the risk of contamination in nucleic acid amplification reactions is minimised by carrying out the reactions in laboratories using separate dedicated areas for sample preparation, nucleic acid amplification, and detection of amplified nucleic acid. It will be appreciated, however, that this is not possible when nucleic acid amplification reactions are carried out away from such facilities (for example in the field, in a physician's office, at home, in remote areas, or in developing countries where specialist facilities may not be available).

The Applicant has appreciated that when a nucleic acid amplification reaction is carried out away from specialised lab facilities, risk of contamination can be reduced by performing the amplification reaction in a processing chamber that is sealed from the external environment. The nucleic acid amplification reaction may be carried out in accordance with a method of the invention. Detection of the amplification product may then be carried out in an analysing chamber that is also sealed from the external environment.

The processing chamber and analysing chamber may be provided by a device. The device may be preloaded with reagents (preferably in lyophilised form) required for amplification of the target nucleic acid (including enzyme activities) and/or detection of the amplification product.

The risk of contamination of other samples with amplification product can be reduced by treatment of the amplification product with nucleic acid modifying or hydrolysing agents that prevent its further amplification. A suitable treatment is chemical treatment that modifies and degrades nucleic acid, for example non-enzymatic degradation of nucleic acid by chemical nucleases. Examples of chemical nucleases are divalent metal chelate complexes, such as copper Phenantroline-Cu (II) or Ascorbate-Cu (II) cleavage, as described by Sigman et al (J. Biol. Chem. (1979) 254, 12269-12272) and Chiou (J. Biochem (1984) 96, 1307-1310). Alternatively, a base that is not naturally present in the target nucleic acid can be incorporated into the amplification product. For example, dUTP can be used to incorporate uracil into a DNA amplification product (as described in U.S. Pat. No. 5,035,996). If, prior to amplification, uracil DNA glycosylase (UDG) is then added to a sample that may have been contaminated with such DNA amplification product this will cause enzymatic hydrolysis of any contaminating amplification product (containing uracil) without affecting natural DNA in the sample.

Reagents required for amplification of the target nucleic acid and/or detection of the amplification product may be provided in lyophilised form. Lyophilisation improves the stability of the reagents, thereby allowing them to be stored for longer periods at higher temperatures. Lyophilisation also reduces the weight and volume of the reagents so that they are easier to transport. Use of lyophilised reagents is, therefore, advantageous for carrying out methods of the invention in the field.

The Applicant has developed lyophilisation formulations (i.e. formulations suitable for lyophilisation) which (once lyophilised) are able to maintain reagents in a stable condition at temperatures up to 37° C. for at least a year. This removes any requirement for cold storage or cold-chain transport of the reagents. The formulations also have the advantage that they can be rapidly rehydrated after lyophilisation. This is a particularly desirable property of lyophilised formulations used for nucleic acid testing in the field since the speed or accuracy of a test can be adversely affected if a reagent required for amplification of a nucleic acid target or detection of amplification product is not rehydrated readily during the amplification or detection method.

According to the invention there is provided a lyophilisation formulation comprising a polysaccharide, a low molecular weight saccharide, and optionally a labile reagent which it is desired to preserve in a stable condition.

The term "labile reagent" is used herein to include any reagent that is susceptible to alteration or degradation when stored in aqueous solution at ambient temperature. Examples of labile reagents include: biomolecules, such as proteins, peptides, or nucleic acids, or derivatives thereof, or chemicals such as enzyme cofactors, enzyme substrates, nucleotide triphosphates (ribo- or deoxyribo-nucleotide triphosphates), or salts. Examples of proteins include enzymes (for example polymerases, such as DNA or RNA polymerases), and antibodies (native or recombinant, and fragments or derivatives thereof that retain antigen binding activity). An antibody (or fragment or derivative) may be present in the formulation in the absence of an antigen bound by the antibody. Examples of nucleic acids include DNA, RNA, nucleic acid primers, and carrier nucleic acid.

The labile reagent may be an amplification reagent for amplifying a target nucleic acid (for example, by a self-sustained amplification reaction), or a detection reagent for detecting product resulting from amplification of target nucleic acid.

The amplification reagent may be any reagent required for amplification of a target nucleic acid. For example the amplification reagent may comprise an enzyme activity, or a primer. The enzyme activity may, for example, be a DNA or RNA polymerase, such as an RNA-dependent DNA polymerase, a DNA-dependent DNA polymerase, a DNA/RNA duplex-specific ribonuclease, or a DNA-dependent RNA polymerase.

In an embodiment of the invention, a lyophilisation formulation of the invention comprises a polysaccharide, a low molecular weight saccharide, and enzyme activities required for self-sustained amplification of a target nucleic acid (for example, using a method of the invention) in the absence of enzyme cofactor(s) (for example magnesium ions), primers, rNTPs, and dNTPs required for specific amplification of the target nucleic acid.

The enzyme activities may be RNA-dependent DNA polymerase, DNA-dependent DNA polymerase, DNA/RNA duplex-specific ribonuclease, and DNA-dependent RNA polymerase enzyme activities.

It will be appreciated that methods of the invention may be carried out in the presence of a polysaccharide and a low molecular weight saccharide (for example, resulting from provision of reagents required for amplification of the target nucleic acid with a lyophilised formulation of the invention).

Examples of suitable polysaccharides are starch, a dextran, or a derivative of a dextran (for example dextran sulphate). The molecular weight of the polysaccharide is typically in the range from about 10-2001 kD, usually 50-100 kD. The polysaccharide may be linear or branched.

The low molecular weight saccharide may be a monosaccharide, disaccharide, or trisaccharide. Examples of suitable disaccharides include trehalose, sucrose, and maltose. Rehydration speeds of formulations of the invention that include trehalose have been found to be particularly fast. Inclusion of trehalose in lyophilised formulations of the invention that comprise an enzyme has been found to maintain the activity of the enzyme for long periods when stored at temperatures up to 37° C.

The low molecular weight saccharide may be present in an amount from 2.5-15% (w/v) of the formulation.

The polysaccharide and low molecular weight saccharide may be present in a total amount of 4-12% (w/v) of the formulation.

A lyophilisation formulation of the invention may further comprise an inert protein such as BSA or casein. BSA can readily be obtained as an RNase-free preparation.

A lyophilisation formulation of the invention may further comprise a sugar-alcohol.

There is also provided according to the invention a lyophilisation formulation of the invention which has been lyophilised (referred to as a lyophilised formulation of the invention). Methods of lyophilisation are known to those of ordinary skill in the art. A suitable method is described in Example 3 below.

Lyophilised formulations of the invention can maintain labile reagents in a stable condition at temperatures of 37° C. for at least a year (FIGS. 5 and 6 show that 100% signal strength is obtained after storage at 37° C. for one year). In contrast, lyophilised formulations described in U.S. Pat. No. 5,556,771 show loss in activity after storage at 35° C. for 61 days (Table 4 of U.S. Pat. No. 5,556,771 shows that the average relative light units (RLU) for "Reagents with DNA target" at 61 days is 90.9% of the average RLU at 0 days). The instructions provided with the SmartMix™ HM of Cepheid (a kit comprising lyophilised reagents for PCR amplifications) specifies that the lyophilised reagents must be stored at 2-8° C. The instructions provided with the commercially available Nuclisens® Basic Kit Amplification Reagents of Biomérieux (a kit containing lyophilised reagents for NASBA-based nucleic acid amplification) specify that the amplification reagents should be stored at ≤−20° C. The instructions provided with the commercially available GEN-PROBE® APTIMA® General Purpose Reagents (GPR) 250 Kit (comprising lyophilised reagents for carrying out transcription-mediated amplification) specifies that the lyophilised reagents should be stored at 2-8° C. Lyophilised formulations of the invention do not need to be refrigerated.

The Applicant has surprisingly found that lyophilised formulations of the invention that comprise an enzyme (for example, an enzyme or combination of enzymes required to carry out a method of the invention) are able to maintain the enzyme(s) in a stable condition even in the absence of (or with little, e.g. <1 mM) buffering agent for the enzyme(s). This has the advantage that lyophilised enzyme formulations are simplified. It may also be advantageous for other lyophilised formulations comprising labile reagents besides enzymes to include little or no buffering agent.

Thus, according to the invention there is provided a lyophilised (or lyophilisation) formulation which comprises a polysaccharide, a low molecular weight saccharide and a labile reagent which it is desired to preserve in a stable condition, wherein the formulation does not include a buffering agent, or the buffering agent is present at a concentration of less than 1 mM.

The term "buffering agent" is used to mean an agent that tends to maintain a solution within a desired pH range (for example a pH range in which an enzyme retains activity). Typically, a weak acid or a weak base is used. Examples of buffering agents used for transcription-based amplification reactions include Tris-based buffers (e.g. Tris-HCl), HEPES, and acetate-based buffers. Phosphate buffering agents are not used for transcription-based amplification reactions because they are inhibitory to the amplification reaction.

According to the invention there is also provided a lyophilised formulation for use in a method of the invention, comprising a polysaccharide, a low molecular weight saccharide, and a labile reagent required for carrying out a method of the invention which it is desired to preserve in a stable condition, wherein the formulation does not include a buffering agent(s) required for the method or the buffering agent is present at a concentration of less than that required for the method. If buffering agent is present, it is preferred that this is at a concentration of less than 25%, preferably less than 10%, of that required for the method, or less than 1 mM.

The labile reagent may be an amplification reagent for amplifying the target nucleic acid or a detection reagent for detecting product resulting from amplification of the target nucleic acid.

In certain embodiments the labile reagent comprises an enzyme or enzymes (for example an RNA-dependent DNA polymerase, a DNA-dependent DNA polymerase, a DNA/RNA duplex-specific ribonuclease, and a DNA-dependent RNA polymerase). Since the amount of enzyme substrate and any cofactor required for activity of the enzyme(s) may vary with different primer/template combinations, it is preferred that such formulations do not include substrates or cofactors for the enzyme or enzymes. It is also preferred that such formulations do not include salt (for example, KCl, NaCl) since this again may vary with different primer/template combinations.

In other embodiments the labile reagent comprises primers for specific amplification of target nucleic acid using a method of the invention. Such formulations preferably further comprise nucleotides and/or an enzyme cofactor required for the method.

We have also found that lyophilised formulations of the invention can be rapidly rehydrated without the need for a specialised reconstitution buffer. It has been found that known lyophilised formulations, for example those described in U.S. Pat. No. 5,556,771, or commercially available lyophilised reagents (from BioMerieux, Gen-Probe, Cepheid), do not reconstitute rapidly, but instead require extensive mixing in specially formulated reconstitution buffers. The instructions provided with the Nuclisens® Basic Kit Amplification Reagents kit referred to above specify that enzyme diluent should be added to the lyophilised enzyme sphere, and left for at least 20 minutes at room temperature. The instructions provided with the SmartMix™ HM kit referred to above specify that the lyophilised beads are rehydrated after adding water by using a vortex. In contrast, lyophilised formulations of the invention reconstitute rapidly (usually in less than 10 seconds in water or other liquid, such as nucleic acid extract) without any requirement for vortexing.

There is also provided according to the invention a kit comprising a plurality of different, separate lyophilised formulations of the invention.

A kit of the invention may comprise reagents required for amplification and/or detection of a target nucleic acid. The reagents may include enzyme activities required for amplification of a target nucleic acid by PCR or by a self-sustained amplification reaction. A kit of the invention may be for amplification of a target nucleic acid using a method of the invention.

In some embodiments of kits of the invention which comprise enzyme activities required for amplification of a target nucleic acid by a self-sustained amplification reaction, the enzyme activities may be in a separate lyophilised formulation to the primers, ribonucleotide triphosphates and deoxyribonucleotide triphosphates (and any enzyme cofactors) required for specific amplification of the target nucleic acid.

A kit of the invention may comprise: i) a first lyophilised formulation of the invention, which includes an RNA-dependent DNA polymerase, a DNA-dependent DNA polymerase, a DNA/RNA duplex-specific ribonuclease, and a DNA-dependent RNA polymerase; and ii) a second lyophilised formulation of the invention, which includes primers for specific amplification of a target nucleic acid, ribonucleotide triphosphates for synthesis of RNA by the DNA-dependent RNA polymerase, and deoxyribonucleotide triphosphates for synthesis of DNA by the RNA- or DNA-dependent polymerase.

The RNA-dependent DNA polymerase and the DNA-dependent DNA polymerase may be provided by a reverse transcriptase, such as reverse transcriptase from Avian Myeloblastosis Virus (AMV) or Moloney Murine Leukemia Virus (MMLV). The DNA/RNA duplex-specific ribonuclease may be provided by RNase H, such as RNase H from E. coli or by the RNase H activity of AMV reverse transcriptase or MMLV reverse transcriptase. The DNA-dependent RNA polymerase may be provided by T7 RNA polymerase. Where AMV or MMLV reverse transcriptase is used, additional DNA/RNA duplex-specific ribonuclease activity may be provided by a separate enzyme (for example E. coli RNase H), as in conventional NASBA, or the activity may be provided solely by the AMV-RT or MMLV-RT.

An enzyme cofactor(s) (such as magnesium ions) required by the enzyme activities for amplification of the target nucleic acid may be provided as a separate component of the kit, or in the first or second lyophilised formulation.

The Applicant has found that an enzyme stored in a lyophilised formulation of the invention can remain stable for long periods at temperatures of 37° C. even if the formulation does not include any reagents (for example, cofactors or substrates) required for amplification of a target nucleic acid using the enzyme. Often the optimal mix of amplification reagents will vary with the target nucleic acid and the particular primers that are used. The applicant has appreciated that if the amplification reagents are lyophilised separately from the enzymes, then a lyophilised enzyme formulation of the invention can be used with any target nucleic acid and primer combinations (i.e. as a universal lyophilised formulation). Since the amount of salt used may also vary with different target nucleic acid and primer combinations, it may also be preferred to exclude salt from such formulations.

Thus, the first lyophilised formulation may not include any amplification reagents (for example, substrates or cofactors) required by the enzyme activities for amplification of the target nucleic acid. The first lyophilised formulation may also not include any salt.

The reverse transcriptase, DNA/RNA duplex-specific ribonuclease, and DNA-dependent RNA polymerase activities may each be provided by separate enzymes (although the reverse transcriptase may also include DNA/RNA duplex-specific ribonuclease activity, for example AMV-RT). This has been found to reduce the complexity of the amplification mixture required to provide optimal enzyme activities at the temperature range of between 42 and 50° C. compared, for example, to use of enzymes (such as MMLV reverse transcriptase) which comprise reverse transcriptase and RNase H activities (without an additional enzyme with DNA/RNA duplex-specific ribonuclease activity).

A kit of the invention for carrying out a method of the invention may further comprise an agent for facilitating or enhancing the self-sustained amplification reaction, for example, any of the agents listed above. The agent may form a separate component of the kit, or the agent may be in the first or second lyophilised formulation.

A kit of the invention for carrying out a method of the invention may further comprise an agent that facilitates primer annealing, for example potassium or sodium ions. The agent may form a separate component of the kit, or the agent may be in the first or second lyophilised formulation.

A kit of the invention for carrying out a method of the invention may further comprise an agent that facilitates denaturation of double stranded nucleic acid during the amplification reaction, for example inosine triphosphate. The agent may form a separate component of the kit, or the agent may be in the first or second lyophilised formulation.

A kit of the invention for carrying out a method of the invention may further comprise an agent that improves specificity of the amplification reaction. The agent may form a separate component of the kit, or the agent may be in the first or second lyophilised formulation.

It may be desirable, however, that a polar aprotic solvent, such as DMSO, is not included as part of a lyophilisation (or lyophilised) formulation of the invention since this can adversely affect lyophilisation. As explained above, a zwitterionic compound, such as betaine, may be used instead of DMSO since betaine does not appear to inhibit lyophilisation.

It has been found that high concentrations of a sugar-alcohol such as mannitol can hinder rehydration of a lyophilised formulation of the invention. Consequently, it may be desired that if a sugar alcohol is included in a lyophilisation (or lyophilised) formulation of the invention, it is present at less than 7.5% (w/v), less than 5% (w/v), or less than 3% (w/v). Alternatively, a sugar alcohol may be excluded from a formulation of the invention.

The first lyophilised formulation may further comprise an inert protein.

The second lyophilised formulation may comprise a polysaccharide, a low molecular weight saccharide, optionally a sugar alcohol, and any (or all) of the following: a reducing agent; positively charged ions; an enzyme cofactor (for example magnesium ions) required for activity of the amplification enzymes.

A kit of the invention may further comprise: iii) a third lyophilised formulation of the invention, which includes a detection reagent for detecting amplification product, and optionally iv) a fourth lyophilised formulation of the invention, which includes a labelling reagent for labelling the detection reagent.

In alternative embodiments, a kit of the invention may comprise: i) a first lyophilised formulation of the invention, which includes a detection reagent for detecting target nucleic acid, or product resulting from amplification of target nucleic acid; and optionally ii) a second lyophilised formulation of the invention, which includes a labelling reagent for labelling the detection reagent.

The detection reagent may be any suitable reagent for detection of amplification product or target nucleic acid. The detection reagent may comprise a detection probe that hybridises to the amplification product or target nucleic acid. The detection reagent may itself be labelled (with one or more labels), thereby enabling direct detection of the amplification product or target nucleic acid utilising the detection reagent. Alternatively, a labelling reagent (which comprises one or more labels) for binding the detection reagent may be provided, thereby enabling indirect detection of the amplification product or target nucleic acid utilising the detection and labelling reagents.

The label(s) of the detection reagent (where this is labelled) or labelling reagent may be a visually detectable label. Examples of visually detectable labels include colloidal metal sol particles, latex particles, or textile dye particles. An example of colloidal metal sol particles is colloidal gold particles.

The detection reagent may be a detection probe that is provided with a plurality of detection ligands (for example biotin), each of which can be bound by a labelling reagent. Each labelling reagent may comprise a plurality of detection ligand binding moieties, each detection ligand binding moiety being capable of binding a detection ligand of the detection reagent. An example of such a labelling reagent is colloidal gold conjugated to antibiotin antibody. An example of the detection probe and labelling reagent is the detector probe and coloured anti-hapten detection conjugate, respectively, described and illustrated in Dineva et al (Journal of Clinical Microbiology, 2005, Vol. 43(8): 4015-4021).

Detection of the amplification product may take place in standard hybridisation buffer. Examples of typical standard hybridisation buffers include a Tris or phosphate buffer comprising salt (suitably 100-400 mM), surfactant (such as PVP), and a detergent.

It has been found that extracted nucleic acid in the elution buffer used in conventional nucleic acid extraction procedures (usually a low molarity buffer, such as Tris, Tris-EDTA, Tris-HCl, or HEPES), or even water, provides a suitable sample solution for carrying out a method of nucleic acid amplification according to the invention. Consequently, if desired a method of nucleic acid amplification of the invention can be carried out simply by contacting the enzyme activities required for self-sustained amplification of target nucleic acid, enzyme cofactor(s) required by the enzyme activities, primers required for specific amplification of target nucleic acid, required NTPs (rNTPs and dNTPs for transcription-based amplifications), and (if appropriate) any of the agents listed above (for example by contacting first and second lyophilised formulations provided in a kit of the invention), with the extracted nucleic acid in elution buffer (or water) and heating to between 42 and 50° C. Detection of amplification product (for example, as described above using a dipstick) can then be carried out simply by contacting the detection reagents with the sample solution at the end of the amplification reaction, and contacting the resulting mixture with a contact end of the dipstick.

In an alternative aspect of the invention there is provided a composition for use in a self-sustained amplification reaction (for example, using a method of the invention), the composition comprising enzyme activities required for self-sustained amplification of a target nucleic acid (for example, using a method of the invention), and:
i) an agent for facilitating or enhancing the self-sustained amplification reaction;
ii) an agent that facilitates primer annealing;
iii) an agent that facilitates denaturation of double stranded nucleic acid; or
iv) an agent that improves specificity of the self-sustained amplification reaction.

The agents (i)-(iv) may be any of the agents listed above.
Combinations of agents may be used, such as: (i)+(ii); (i)+(iii); (i)+(iv); (ii)+(iii); (ii)+(iv); (iii)+(iv); (i)+(ii)+(iii); (i)+(ii)+(iv); or (i)+(iii)+(iv).

Use of such agents may improve the reliability, robustness (for example to temperature fluctuations), specificity and/or sensitivity of the amplification reaction. The Applicant has surprisingly found that use of an inert protein, and an inert amphiphilic polymer (which is not a protein) is particularly effective.

The composition may comprise enzyme activities required for self-sustained amplification of a target nucleic acid (for example using a method of the invention), an inert protein, and an inert amphiphilic polymer (which is not a protein). The composition may further comprise an agent that facilitates primer annealing and/or an agent that facilitates denaturation of double stranded nucleic acid and/or an agent that improves specificity of an amplification reaction. The agent(s) may be any of the agents listed above.

In a further aspect of the invention there is provided a composition for self-sustained amplification of a target nucleic acid (for example using a method of the invention), which comprises: enzyme activities required for self-sustained amplification of a target nucleic acid (for example using a method of the invention); primers for specific amplification of the target nucleic acid; nucleotide triphosphates required for extension of the primers (deoxyribonucleotide triphosphates and ribonucleotide triphosphates are required for transcription-based amplification); and any of the following agents:
i) an agent for facilitating or enhancing the self-sustained amplification reaction;
ii) an agent that facilitates primer annealing;
iii) an agent that facilitates denaturation of double stranded nucleic acid; or
iv) an agent that improves specificity of the self-sustained amplification reaction.

The agents (i)-(iv) may be any of the agents listed above.
Again, combinations of agents may be used, such as: (i)+(ii); (i)+(iii); (i)+(iv); (ii)+(iii); (ii)+(iv); (iii)+(iv); (i)+(ii)+(iii); (i)+(ii)+(iv); or (i)+(iii)+(iv). Use of an inert protein, and an inert amphiphilic polymer (which is not a protein) is particularly effective.

The composition for self-sustained amplification of a target nucleic acid may comprise: enzyme activities required for self-sustained amplification of the target nucleic acid; primers for specific amplification of the target nucleic acid;

nucleotide triphosphates required for extension of the primers (deoxyribonucleotide triphosphates and ribonucleotide triphosphates are required for transcription-based amplification); an inert protein; and an inert amphiphilic polymer (which is not a protein).

The composition may further comprise an agent that facilitates primer annealing and/or an agent that facilitates denaturation of double stranded nucleic acid and/or an agent that improves specificity of an amplification reaction. The agent(s) may be any of the agents listed above.

The enzyme activities of a composition of the invention may be: an RNA-dependent DNA polymerase, a DNA-dependent DNA polymerase, a DNA/RNA duplex-specific ribonuclease, and a DNA-dependent RNA polymerase.

A composition of the invention may further comprise a buffer required for the enzyme activities to carry out amplification of the target nucleic acid in the presence of the primers, dNTPs, and rNTPs. Examples of suitable buffers include Tris-HCl, HEPES, and acetate buffers.

A composition of the invention may further comprise any necessary cofactors required by the enzyme activities.

A composition of the invention may further comprise a low molecular weight saccharide and/or a sugar-alcohol. Alternatively, a composition of the invention may further comprise a polysaccharide and a low molecular weight saccharide and/or a sugar alcohol. This may be particularly suitable if the composition is lyophilised.

It will be appreciated that components of a composition of the invention can be provided in the form of a kit in which one or more components of the composition are separate from remaining components of the composition. Mixing of the separate components then provides a composition of the invention.

The enzyme activities required for amplification of the target nucleic acid may be separate from the primers, NTPs, and any cofactors required by the enzyme activities.

Thus, there is also provided according to the invention a kit for amplification of a target nucleic acid by a self-sustained amplification reaction (for example, carried out using a method of the invention), which comprises:
i) a first composition comprising enzyme activities required for amplification of the target nucleic acid by the self-sustained amplification reaction; and separately
ii) a second composition comprising primers for specific amplification of a target nucleic acid, NTPs required for extension of the primers (ribonucleotide triphosphates and deoxyribonucleotide triphosphates are required for transcription-based methods); and any of the following agents:
a) an agent for facilitating or enhancing the self-sustained amplification reaction;
b) an agent that facilitates primer annealing;
c) an agent that facilitates denaturation of double stranded nucleic acid;
d) an agent that improves specificity of the self-sustained amplification reaction.

The agent(s) may be a further separate component of the kit, or the agent(s) may be in the first or second composition.

The agents (a)-(d) may be any of the agents listed above. The first composition may comprise an inert protein and/or the second composition may comprise a reducing agent and/or a sugar alcohol or low molecular weight saccharide.

The enzyme activities may be an RNA-dependent DNA polymerase, a DNA-dependent DNA polymerase, a DNA/RNA duplex-specific ribonuclease, and a DNA-dependent RNA polymerase.

The kit may further comprise a cofactor(s) required by the enzyme activities. The cofactor(s) may be provided as a separate component of the kit or with the first or second composition.

A kit of the invention may further comprise an enzyme buffer required for the enzyme activities to carry out amplification of the target nucleic acid in the presence of the primers, dNTPs, and rNTPs. Examples of suitable buffers include Tris-HCl, HEPES, and acetate buffers. The enzyme buffer may be provided as a separate component of the kit or with the first or second formulation or composition.

For those embodiments of the invention in which detection of the amplification product is carried out using a dipstick, a kit of the invention may further comprise a dipstick capable of transporting a solution by capillarity.

A kit of the invention may further comprise instructions for carrying out a method of nucleic acid amplification and/or detection using the kit.

It may be desired to include with one or more separate components of a kit of the invention a dye. For example, the separate components may comprise different coloured dyes so that the different formulations or compositions of the kit can readily be distinguished from each other. This can help reduce the risk of adding formulations or compositions to sample solution in the wrong order, or ensure correct pre-loading of a device to carry out a method of the invention. Suitable dyes include food dyes or textile dyes. These should be added at a concentration that is not inhibitory to amplification or detection. For example, concentrations of 0.2% may be used.

It will generally be desirable to include with a formulation, composition, or kit of the invention an RNase inhibitor.

The components of a kit of the invention may be provided in a device for carrying out a method of nucleic acid amplification and optionally detection of nucleic acid product of the amplification reaction, the device being preloaded with the components.

Methods of the invention have been found to provide improved specificity of amplification of target nucleic acid, and reduced background, compared to conventional self-sustained amplification methods.

Methods of the invention are simpler and faster than conventional methods, and can be carried out without use of specialised lab facilities or instruments. We have also found that methods of the invention are more tolerant to temperature fluctuations than conventional NASBA methods (some methods of the invention are tolerant to temperature fluctuations of +/−4° C., compared with only +/−0.5° C. for conventional NASBA). Consequently, methods of the invention are particularly suited for use in the field, in a physician's office, at home, in remote areas, or in developing countries where specialist facilities and equipment may not be available.

Lyophilised formulations of the invention are stable for long periods at ambient temperature and can be used to provide reagents required for methods of the invention. Because there is no need to store the lyophilised formulations at low temperatures, or to transport them by cold-chain transport, kits can be provided for carrying out methods of the invention in the field.

Reagents required for methods of the invention may be provided preloaded in a device comprising separate processing and analysing chambers that are sealed from the external environment. The chambers are preferably arranged so that processed sample (i.e. sample which has been incubated under conditions for amplification in the processing chamber) can be passed into the analysing chamber without exposure to the external environment. Such devices reduce contamination of the amplification reaction, and thereby minimise the possibility of false positive results. This allows nucleic acid amplification reactions to be carried out without the need for designated separate areas for sample preparation, amplification, and detection, and facilitates use of methods of the invention in the field.

In certain aspects of the invention it may be desired to carry out a self-sustained nucleic acid amplification reaction at a temperature that is lower than the range of between 42° C. and 50° C. (for example in the range 35-41° C.), but take advantage of other preferred aspects of the invention. The preferred aspects may include, for example, any of the following: use of one or more of the agents that facilitate or enhance the self-sustained amplification reaction, or that facilitate primer annealing or denaturation of double stranded DNA, or that improve the specificity of the amplification reaction; use of compositions or lyophilised formulations of the invention for the amplification reaction; carrying out the amplification reaction in the presence of a polysaccharide and a low molecular weight saccharide; performing the amplification reaction in a processing chamber that is sealed from the external environment (and optionally detecting amplified product in an analysing chamber sealed from the external environment); detecting amplified product using visually detectable labels.

There is also provided according to the invention a primer or probe that comprises or consists of a sequence recited in any of SEQ ID NOs: 1 to 9.

The primers or probes of the invention may be up to 50, 40, or 30 nucleotides in length.

There is further provided according to the invention a set of primers that comprises a primer with sequence recited in SEQ ID NO: 1 and a primer with sequence recited in SEQ ID NO: 2.

There is further provided according to the invention a set of primers and probes that comprises: a primer with sequence recited in SEQ ID NO: 1; a primer with sequence recited in SEQ ID NO: 2; a probe with sequence recited in SEQ ID NO: 3; a probe with sequence recited in SEQ ID NO: 4; and a probe with sequence recited in SEQ ID NO: 5.

The set may be used for amplification and/or detection of HIV-1 RNA.

There is further provided according to the invention a set of primers that comprises a primer with sequence recited in SEQ ID NO: 6 and a primer with sequence recited in SEQ ID NO: 7.

There is further provided according to the invention a set of primers and probes that comprises: a primer with sequence recited in SEQ ID NO: 6; a primer with sequence recited in SEQ ID NO: 7; a probe with sequence recited in SEQ ID NO: 8; and a probe with sequence recited in SEQ ID NO: 9.

The set may be used for amplification and/or detection of *Chlamydia trachomatis* RNA.

Embodiments of the invention are described in the following examples, with reference to the accompanying drawings in which:

FIG. 3 shows the results of amplification and detection of HIV RNA using a method according to an embodiment of the invention;

FIG. 4 shows the results of amplification and detection of *Chlamydia trachomatis* RNA using a method according to a further embodiment of the invention FIG. 5 shows the results of amplification and detection of HIV RNA using a method according to a further embodiment of the invention in comparison with results obtained from use of a commercially available NASBA test;

Figure 1:
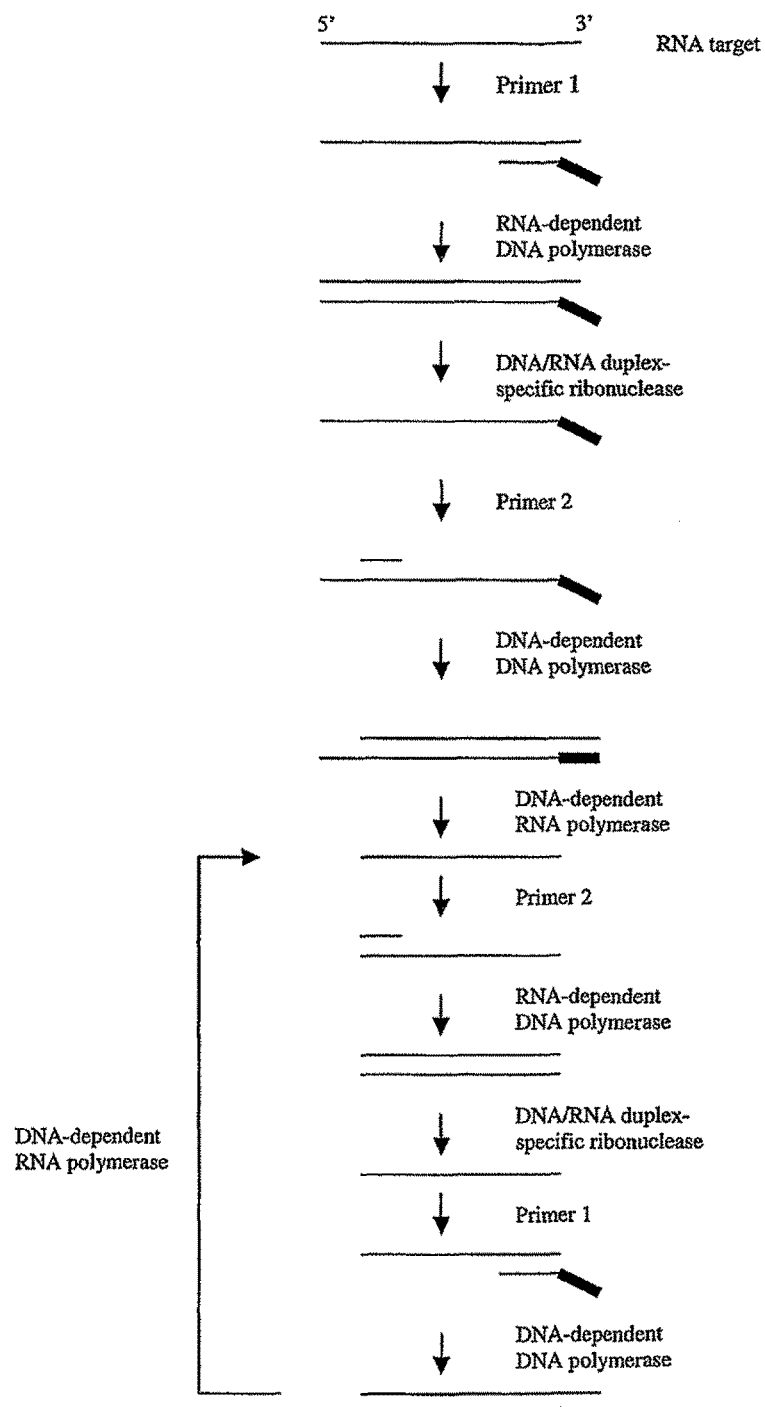
FIG. 1 shows schematically the steps in transcription-based amplification of a target RNA.

EXAMPLE 1 a) Testing for HIV RNA

This example describes amplification and detection of HIV-1 RNA using an embodiment of the invention (referred to as Simple AMplification BAsed-Nucleic Acid Testing (SAMBA-NAT)). The method steps are explained below.
Lyophilised Formulations:

Lyophilised Bead A: 1 mM dNTP, 2 mM rATP, 2 mM rCTP, 2 mM rUTP, 1.5 mM rGTP, 0.5 mM rITP, 12 mM $MgCl_2$, 70 mM KCl, 5 mM DTT, 10 units RNase inhibitor, 250 mM sorbitol, 1.5% dextran, 8.75% trehalose, and 0.2 mM primers;

Lyophilised Bead B: 6.4 units AMV Reverse transcriptase, 0.16 units RNAse H, 32 units T7 RNA polymerase, 10 units RNase inhibitor, 1.5% (w/v) dextran, 8.75% (w/v) trehalose, 2 µg BSA;

Lyophilised Bead C: colloidal gold particles conjugated with anti-biotin antibody by passive absorption at a rate of 6 µg/OD(520 nm)/ml (referred to as "gold conjugate"), 1.5% dextran, 8.75% trehalose, 1% casein;

Lyophilised Bead D: $5 \times 10^{11}$ copies of detector probe (see below), $10^{12}$ copies of helper probe (see below), 1.5% dextran, 8.75% trehalose.

Detection buffer: Standard Tris based hybridization buffer (pH 8.5) comprising salt, detergent and BSA or powdered milk with 0.05% sodium azide.
Primers and Probes:

Sense primer 5' CCT CAA TAA AGC TTG CCT TGA (SEQ ID NO: 1) and antisense primer 5' GGC GCC ACT GCT AGA GA (SEQ ID NO: 2) elongated at 5'-end with T7 promoter sequence.

```
Detector probe:
5' CTC AAT AAA GCT TGC CTT GA      (SEQ ID NO: 3)

Capture probe:
5' CGT CTG TTG TGT GAC TCT GG      (SEQ ID NO: 4)

Helper probe:
5' GTG CTT CAA GTA GTG TGT GCC     (SEQ ID NO: 5)
```

The detector and capture probes are prepared as described before (Dineva et al, Journal of Clinical Microbiology, 2005, Vol. 43(8): 4015-4021).

DNA probes (20-25 nucleotides long) with sequence complementary to sequence of the target nucleic acid at a region adjacent to the region complementary to the capture probe sequence could also be used as previously described in WO 02/04668.

Dipstick: a strip of nitrocellulose membrane comprising: a contact end for contacting sample solution containing amplification product; and a capture zone for capturing amplification product. The capture probe is immobilised to the capture zone as described by Dineva et al (Journal of Clinical Microbiology, 2005, Vol. 43(8): 4015-4021).

Method Steps:

Step 1: 200 ul of samples containing different amounts of HIV-1 RNA ($10^5$, $10^4$, $5\times10^3$, $10^3$, $5\times10^2$, $2\times10^2$ copies/ml) (and a control containing no HIV-1 RNA) were extracted using a Roche High Pure Viral Nucleic Acid Kit or a Qiagen QIAamp Viral RNA Kit by following instructions of the manufacturer.

Step 2: 50 μl sample extract from step 1 was added to lyophilised Bead A and mixed;

Step 3: the solution from step 2 was incubated at 45° C. for 5 minutes;

Step 4: lyophilised Bead B was added to the solution from step 3 and mixed;

Step 5: the solution from step 4 was incubated at 45° C. for 45 minutes;

Step 6: 200 μl detection buffer was added to the solution from step 5;

Step 7: lyophilised Beads C and D were added to the solution from step 6 and mixed;

Step 8: 100 μl of the solution from step 7 was contacted with the contact end of the dipstick. The solution travels up the dipstick by capillary action to a capture zone of the dipstick. If amplification product is present in the solution, this is bound by the detector probe provided with Bead D. The biotin moieties of the detector probe are bound by the gold conjugate provided with Bead C. Amplification product bound to the detector probe and gold conjugate is captured at the capture zone by hybridisation of the amplification product to the immobilised capture probe. Gold conjugate bound to the biotin moieties of the detector probe provides a visible signal at the capture zone if the amplification product has been captured by the capture probe;

Step 9: any signal appearing at the capture zone of the dipstick was read.

The procedure from sample preparation to signal reading was completed in 80 minutes. The results for each of the different samples are shown in FIG. 3, and demonstrate that as few as 200 copies of the RNA target nucleic acid were detected using this procedure.

b) Testing for *Chlamydia trachomatis* RNA

Figure 2:
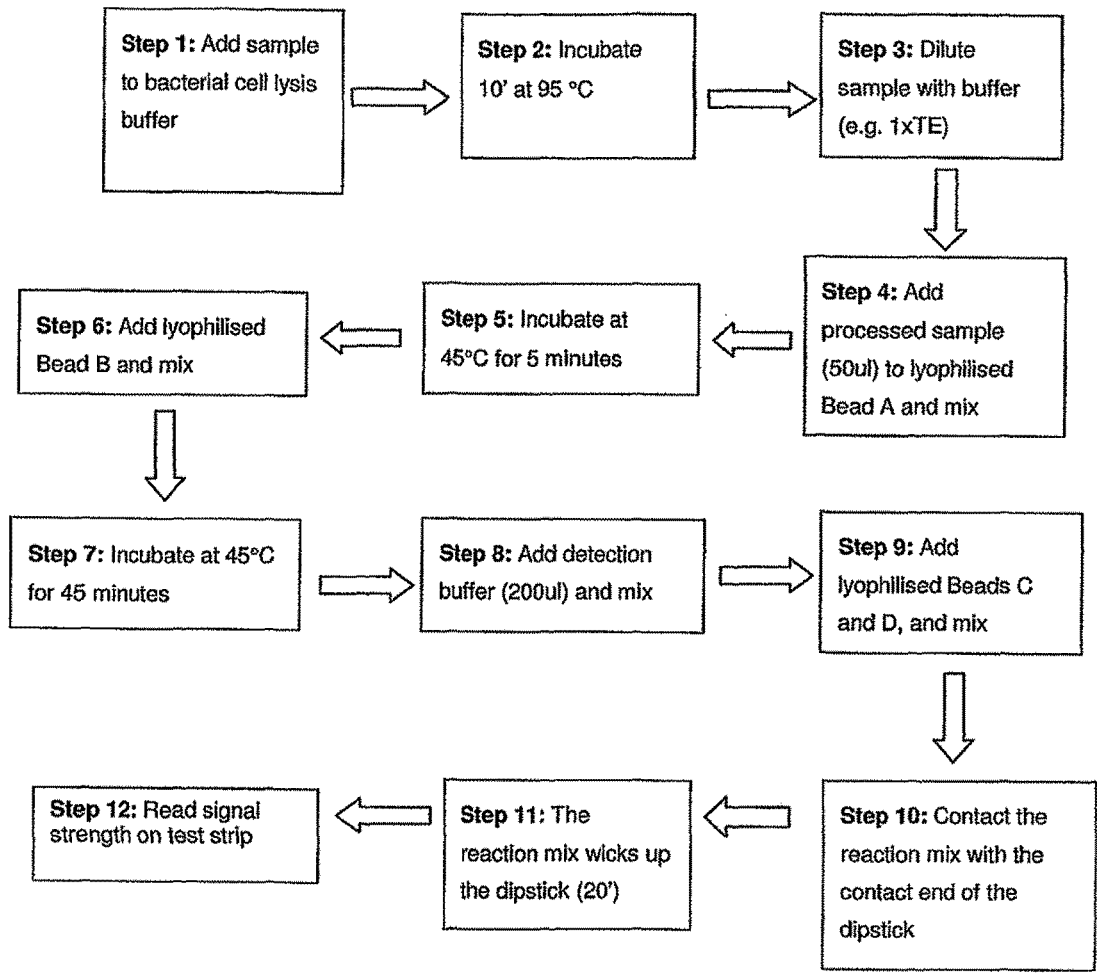
FIG. 2 illustrates steps of a method according to an embodiment of the invention.

The testing procedure for *Chlamydia trachomatis* is as shown in FIG. 2 and similar to that for HIV RNA testing as described above with the exception of the primers and probes used, which have the following 16S rRNA specific sequences:

Sense primer 5' AGC AAT TGT TTC GAC GAT TG (SEQ ID NO: 6) and antisense primer 5' CA CAT AGA CTC TCC CTT AAC (SEQ ID NO: 7) elongated at 5'-end with T7 promoter sequence;

```
Detector probe:
5' AAC TTG GGA ATA ACG GTT GGA A    (SEQ ID NO: 8)

Capture probe:
5' CGC TAA TAC CGA ATG TGG CGA      (SEQ ID NO: 9)
```

The results are shown in FIG. 4. As few as 50 copies of the target nucleic acid were detected.

EXAMPLE 2

Comparison of Detection of HIV RNA Using SAMBA-NAT and NASBA-NAT

Detection of $10^5$, $10^4$, $10^3$, or $2\times10^2$ copies/ml of HIV RNA using a SAMBA-NAT method similar to that described in Example 1 was compared with amplification using a commercially available NASBA kit: NucliSens Basic Kit Amplification Reagents, Biomerieux (referred to as NASBA-NAT). For the NASBA-NAT this requires two additional incubation steps prior to addition of enzyme mixture and amplification: a) incubation at 65° C. for 5 minutes, followed by b) incubation at 41° C. for 5 minutes. Amplicons prepared by either SAMBA-NAT or NASBA-NAT methods were detected using an equivalent dipstick detection procedure to that described in Example 1. The results are shown in FIG. 5, and demonstrate that the SAMBA-NAT method detects HIV RNA with equivalent sensitivity to the NASBA-NAT method. It can be seen from the zero (control) lane that the NASBA-NAT method provides a background signal. In contrast, no background signal is present in the SAMBA-NAT control lane. It is concluded from this that the SAMBA-NAT method has higher specificity and reduced background interference compared to the NASBA-NAT method. The SAMBA-NAT method was also faster than the NASBA-NAT method (45 minutes compared with 90 minutes).

The SAMBA amplification method described in this example has been found to be more tolerant to temperature fluctuations than the conventional NASBA amplification method. Conventional NASBA does not tolerate temperature fluctuations exceeding +/−0.5° C. of the optimal amplification temperature of 41° C. In contrast, the SAMBA method is tolerant to temperature fluctuations of +/−4° C.

Table 1 below summarises some of the main advantages of the SAMBA amplification method over the conventional NASBA amplification method.

TABLE 1

| NASBA Disadvantage | SAMBA Advantage |
| --- | --- |
| Sensitive to temperature fluctuations exceeding +/−0.5° C. | Tolerant to temperature fluctuations of +/−4° C. |
| Three incubation steps and at least two different incubation temperatures | Single incubation temperature |
| Reagents required to be stored at −20° C. and transported by cold-chain transport | Reagents stable above 30° C. |
| More than 10 individually packed reagents required | Only two lyophilised formulations for amplification |
| Amplification time is approximately 90 minutes | Amplification time is approximately 45 minutes |

EXAMPLE 3

Long-term Stability of Enzymes in Lyophilised Formulations

Figure 6:
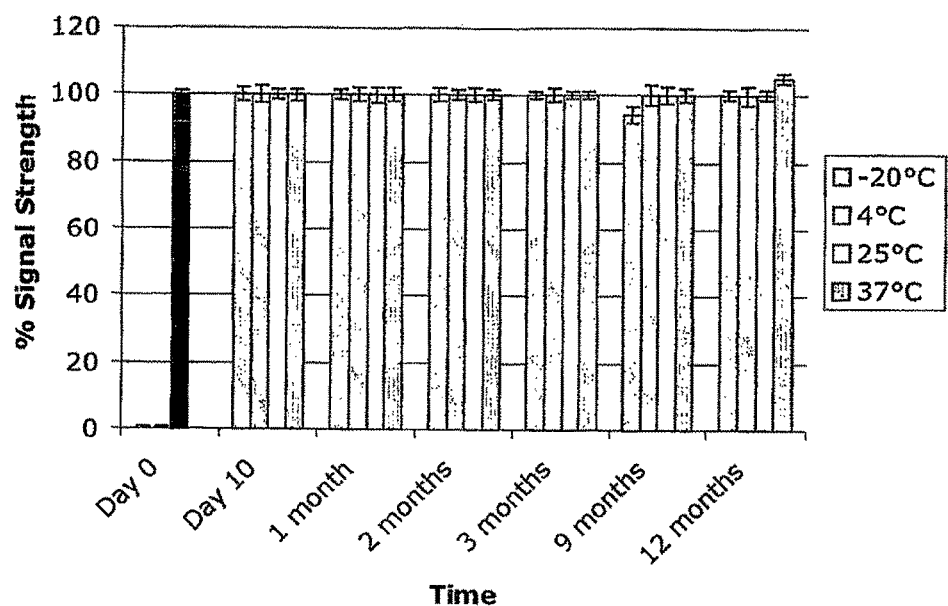
FIG. 6 shows the results of a stability study carried out on lyophilised formulations in accordance with a further embodiment of the invention.

An aqueous solution comprising 1.5% dextran, 8.75% trehalose, 6.4 U AMV Reverse transcriptase, 0.16 U RNAse H, 32 U of T7 RNA polymerase and 2 μg BSA was prepared and then split into several aliquots, each of 25 μl. Each aliquot was lyophilised by dispensing the aqueous solution into cryogenic liquid nitrogen. The solution freezes as discrete spherical particles upon contact with the cryogenic agent. The frozen particles are further subjected to a vacuum while still frozen under pressure (~0.1 mbar) and for time (20-48 hours) sufficient to remove the solvent using freeze drier machine (Christ Alpha 2-4, Martin Christ GmbH, Osterode am Harz, Germany). The lyophilised aliquots were then stored at −20° C., 4° C., 25° C., or 37° C. Lyophilised aliquots stored at each of the different temperatures were tested after intervals of 10 days, 1 month, 2 months, 3 months, 9 months, and 12 months to determine the stability of the enzymes in the lyophilised aliquots. Stability was tested by carrying out amplification of a nucleic acid target, and detection of the amplified product using a method similar to that described in Example 1. The detection signal obtained from each aliquot was compared to that obtained using a freshly made up sample. The results are shown in FIG. 6, and demonstrate that the enzymes remained active after being stored for 12 months at temperatures up to 37° C.

EXAMPLE 4

Long-term Stability of Other Labile Reagents in Lyophilised Formulations

Figure 7:
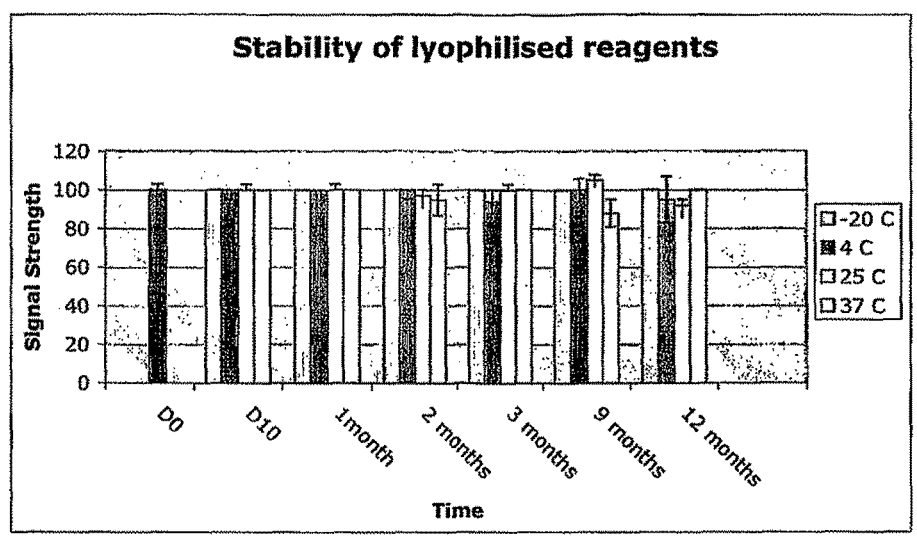
FIG. 7 shows the results of a stability study carried out on lyophilised formulations in accordance with a further embodiment of the invention.

An aqueous solution comprising 2 mM dNTP, 4 mM rATP, 4 mM rCTP, 4 mM rUTP, 3 mM rGTP, 1 mM rITP, 24 mM $MgCl_2$, 140 mM KCl, 10 mM DTT, 10 units RNase inhibitor, 500 mM sorbitol, 1.5% dextran, 8.75% trehalose, and primers was prepared and then split into several aliquots, each of 25 μl. Each aliquot was lyophilised by the method as described in Example 3. The lyophilised aliquots were then stored at −20° C., 4° C., 25° C., or 37° C. Lyophilised aliquots stored at each of the different temperatures were tested after intervals of 10 days, 1 month, 2 months, 3 months, 9 months, and 12 months to determine the stability of the reagents in the lyophilised aliquots. Stability was tested by carrying out amplification of a nucleic acid target, and detection of the amplified product using a method similar to that described in Example 1. The detection signal obtained from each aliquot was compared to that obtained using a freshly made up sample. The results are shown in FIG. 7, and demonstrate that the reagents remained stable after being stored for 12 months at temperatures up to 37° C.

EXAMPLE 5

Rehydration Speed of Lyophilised Formulations

Aqueous solutions were made up (final volume 25 μl) containing dextran, and either sucrose, trehalose, mannitol, or trehalose and mannitol (at various different concentrations). The solutions were then lyophilised using a similar method as that described in Example 3. Water (50 μl) was added to each lyophilised formulation in turn, and the tube containing the formulation was flicked with a finger until rehydration had occurred. The time taken for rehydration (number of flicks, ~1 flick/second) was recorded. The results are shown in Table 2 below.

The results demonstrate that the fastest rehydration times are obtained with lyophilised formulations comprising dextran and trehalose, although rehydration times with dextran and sucrose are nearly as fast. Presence of higher concentrations of mannitol (i.e. 7.5 mM or higher) appears to inhibit rehydration times.

TABLE 2

| Formulation | Reagents | Final concentration (mM) | Rehydration time (arbitrary units) |
|---|---|---|---|
| A | Dextran | 1.5 | 3-4 |
|   | Sucrose | 7.5 |   |
| B | Dextran | 1.5 | 4 |
|   | Sucrose | 8.75 |   |
| C | Dextran | 1.5 | 5-6 |
|   | Sucrose | 10.5 |   |
| D | Dextran | 1.5 | 3 |
|   | Trehalose | 7.5 |   |
| E | Dextran | 1.5 | 3 |
|   | Trehalose | 8.75 |   |

TABLE 2-continued

| Formulation | Reagents | Final concentration (mM) | Rehydration time (arbitrary units) |
|---|---|---|---|
| F | Dextran | 1.5 | 3-4 |
|   | Trehalose | 10.5 |   |
| G | Dextran | 1.5 | 18-20 |
|   | Mannitol | 7.5 |   |
| H | Dextran | 1.5 | 20 |
|   | Mannitol | 8.75 |   |
| I | Dextran | 1.5 | 26-27 |
|   | Mannitol | 10.5 |   |
| J | Dextran | 1.5 | 3-4 |
|   | Mannitol | 2.5 |   |
|   | Trehalose | 8.75 |   |
| K | Dextran | 1.5 | 16-17 |
|   | Mannitol | 7.5 |   |
|   | Trehalose | 8.75 |   |

EXAMPLE 6

Accelerated Stability Study of Enzymes in Lyophilised Formulations

Aliquots of lyophilised enzymes prepared as described in Example 3 were stored at 25° C., 37° C. or 55° C. Lyophilised aliquots stored at each of the different temperatures were tested as described in Example 3 after intervals of 3, 7, 14, 21 days and 1 month to determine the stability of the enzymes in the lyophilised aliquots at elevated temperature. The results obtained demonstrate that the enzymes remained active after being stored for 1 month even at 55° C.

EXAMPLE 7

Figure 8:
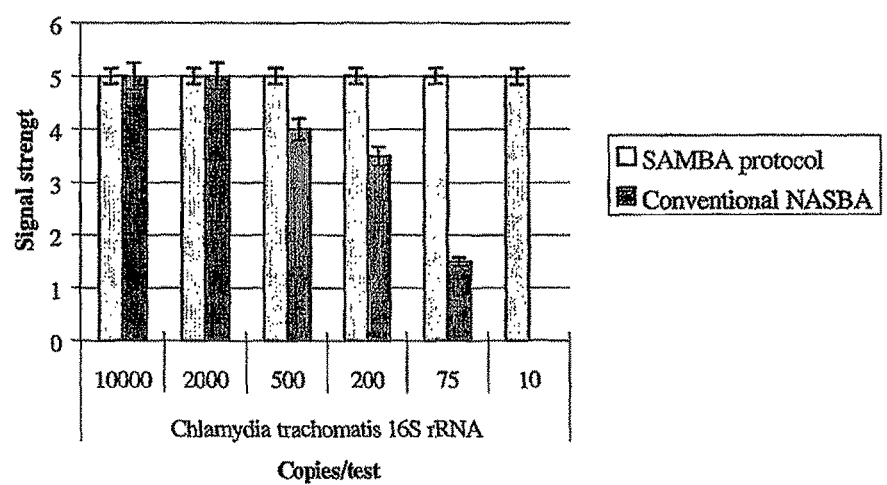
FIG. 8 shows the results of amplification and detection of *Chlamydia trachomatis* RNA using a method according to an embodiment of the invention in comparison with results obtained from use of a commercially available NASBA test.

Comparison of Detection of *Chlamydia trachomatis* 16S rRNA Using of SAMBA-NAT and Conventional NASBA Detection of $10^4$, $2 \times 10^3$, $5 \times 10^2$, $2 \times 10^2$, 75 or 10 copies/test of *Chlamydia trachomatis* 16S rRNA using the SAMBA-NAT method as described in Example 1(b) was compared with detection using conventional NASBA (which requires two additional incubation steps prior to addition of enzyme mixture and amplification: a) incubation at 65° C. for 5 minutes, followed by b) 5 minutes cooling at 41° C.). Amplicons prepared by either SAMBA-NAT or conventional NASBA methods were detected using an equivalent dipstick detection procedure to that described in Example 1. The results are shown in Table 3 below, and FIG. 8, and demonstrate that the SAMBA amplification protocol detects *Chlamydia trachomatis* 16S rRNA with more than 7.5 times increased detection sensitivity than the more complex conventional NASBA method.

TABLE 3

| Copies/test of *Chlamydia trachomatis* 16S rRNA | SAMBA | NASBA |
|---|---|---|
| 10000 | 5 | 5 |
| 2000 | 5 | 5 |
| 500 | 5 | 4 |
| 200 | 5 | 3.5 |
| 75 | 5 | 1.5 |
| 10 | 5 | 0 |

The invention claimed is:

1. A universal lyophilised formulation comprising a polysaccharide, a low molecular weight saccharide, and enzyme activities required for carrying out a self-sustained amplification reaction, wherein the enzyme activities are provided by one or more enzymes, and wherein the formulation does not include cofactors or substrates required for amplification of a target nucleic acid using the enzyme activities.

2. A formulation according to claim 1, which does not include salt.

3. A formulation according to claim 1 or 2, wherein the polysaccharide is a dextran or a dextran derivative.

4. A formulation according to any of claims 1 to 3, wherein the low molecular weight saccharide is trehalose, sucrose, or maltose.

5. A lyophilised formulation comprising a polysaccharide, a low molecular weight saccharide, and enzyme activities required for carrying out a self-sustained amplification reaction, wherein the enzyme activities are provided by one or more enzymes, and wherein the formulation does not include a buffering agent.

6. A formulation according to claim 5, wherein the polysaccharide is a dextran or a dextran derivative.

7. A formulation according to claim 5 or 6, wherein the low molecular weight saccharide is trehalose, sucrose, or maltose.

8. A formulation according to claim 5, wherein the enzyme activities comprise an RNA-dependent DNA polymerase, a DNA-dependent DNA polymerase, a DNA/RNA duplex-specific ribonuclease, and a DNA-dependent RNA polymerase.

9. A formulation according to claim 5, which does not include substrates or cofactors for the enzyme activities.

10. A formulation according to claim 9, which does not include salt.

11. A kit comprising a plurality of different, separate lyophilised formulations wherein each lyophilised formulation is a lyophilised formulation according to claim 1 or 5.

12. A universal lyophilised formulation comprising a polysaccharide, a low molecular weight saccharide, and enzyme activities required for carrying out a self-sustained amplification reaction, wherein the enzyme activities are provided by one or more enzymes, and wherein the formulation does not include cofactors or substrates required for amplification of a target nucleic acid using the enzyme activities, and wherein the formulation does not include a buffering agent, or the buffering agent is present at a concentration of less than 1 mM.

13. A universal lyophilized formulation according to claim 1, wherein the enzyme activities comprise an RNA-dependent DNA polymerase, a DNA-dependent DNA polymerase, a DNA/RNA duplex-specific ribonuclease, and a DNA-dependent RNA polymerase.

14. A universal lyophilized formulation according to claim 12, wherein the enzyme activities comprise an RNA-dependent DNA polymerase, a DNA-dependent DNA polymerase, a DNA/RNA duplex-specific ribonuclease, and a DNA-dependent RNA polymerase.

* * * * *